(12) United States Patent
Boehm

(10) Patent No.: US 7,815,934 B2
(45) Date of Patent: Oct. 19, 2010

(54) SEQUESTERING SUBUNIT AND RELATED COMPOSITIONS AND METHODS

(75) Inventor: Garth Boehm, Westfield, NJ (US)

(73) Assignee: Alpharma Pharmaceuticals, LLC, Bridgewater, NJ (US)

(*) Notice: Subject to any disclaimer, the term of this patent is extended or adjusted under 35 U.S.C. 154(b) by 1542 days.

(21) Appl. No.: 10/667,676

(22) Filed: Sep. 22, 2003

(65) Prior Publication Data

US 2004/0131552 A1    Jul. 8, 2004

Related U.S. Application Data

(60) Provisional application No. 60/412,208, filed on Sep. 20, 2002.

(51) Int. Cl.
*A61K 9/20* (2006.01)
*A61K 9/28* (2006.01)
*A61K 9/48* (2006.01)

(52) U.S. Cl. .................. 424/451; 424/463; 424/464; 424/474

(58) Field of Classification Search .................. None
See application file for complete search history.

(56) References Cited

U.S. PATENT DOCUMENTS

| | | | |
|---|---|---|---|
| 3,493,657 A | 2/1970 | Lewenstein et al. |
| 3,773,955 A | 11/1973 | Pachter et al. |
| 3,845,770 A | 11/1974 | Theeuwes et al. |
| 3,879,555 A | 4/1975 | Pachter et al. |
| 4,088,864 A | 5/1978 | Theeuwes et al. |
| 4,457,933 A | 7/1984 | Gordon et al. |
| 4,582,835 A | 4/1986 | Lewis et al. |
| 4,606,909 A | 8/1986 | Bechgaard et al. |
| 4,795,327 A | 1/1989 | Gaylord et al. |
| 4,834,965 A | 5/1989 | Martani et al. |
| 4,844,907 A | 7/1989 | Elger et al. |
| 4,867,987 A | 9/1989 | Seth |
| 4,871,546 A | 10/1989 | Feltz et al. |
| 5,149,538 A | 9/1992 | Granger et al. |
| 5,236,714 A | 8/1993 | Lee et al. |
| 5,266,331 A | 11/1993 | Oshlack et al. |
| 5,376,384 A | 12/1994 | Eichel et al. |
| 5,451,408 A | 9/1995 | Mezei et al. |
| 5,478,573 A | 12/1995 | Eichel et al. |
| 5,508,042 A | 4/1996 | Oshlack et al. |
| 5,529,790 A | 6/1996 | Eichel et al. |
| 5,549,912 A | 8/1996 | Oshlack et al. |
| 5,580,578 A | 12/1996 | Oshlack et al. |
| 5,614,218 A | 3/1997 | Olsson et al. |
| 5,629,011 A | 5/1997 | Illum |
| 5,639,476 A | 6/1997 | Oshlack et al. |
| 5,656,295 A | 8/1997 | Oshlack et al. |
| 5,672,360 A | 9/1997 | Sackler et al. |
| 5,725,883 A | 3/1998 | Staniforth et al. |
| 5,834,024 A | 11/1998 | Heinicke et al. |
| 5,866,164 A | 2/1999 | Kuczynski et al. |
| 5,935,975 A | 8/1999 | Rose et al. |
| 5,968,551 A | 10/1999 | Oshlack et al. |
| 6,033,687 A | 3/2000 | Heinicke et al. |
| 6,103,261 A | 8/2000 | Chasin et al. |
| 6,143,353 A | 11/2000 | Oshlack et al. |
| 6,214,385 B1 | 4/2001 | Heinicke et al. |
| 6,228,863 B1 | 5/2001 | Palermo et al. |
| 6,277,384 B1 | 8/2001 | Kaiko et al. |
| 6,316,031 B1 | 11/2001 | Oshlack et al. |
| 6,375,957 B1 | 4/2002 | Kaiko et al. |
| 6,475,494 B2 | 11/2002 | Kaiko et al. |
| 6,495,120 B2 | 12/2002 | McCoy et al. |
| 6,627,635 B2 | 9/2003 | Palermo et al. |
| 6,635,277 B2 | 10/2003 | Sharma et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 6,872,407 B2 | 3/2005 | Notario et al. |
| 7,056,532 B1 | 6/2006 | Kabanov et al. |
| 7,081,255 B2 | 7/2006 | Baert et al. |
| 7,101,574 B1 | 9/2006 | Criere et al. |
| 7,125,561 B2 | 10/2006 | Sackler et al. |

(Continued)

FOREIGN PATENT DOCUMENTS

CA    2229621    3/1998

(Continued)

OTHER PUBLICATIONS

RX-list: Embeda(Morphine Sulfate and Naltrexone Hydrichloride Extended release Capsules, Aug. 27, 2009.*

(Continued)

*Primary Examiner*—Carlos A Azpuru
(74) *Attorney, Agent, or Firm*—Patrick J. Halloran; G. Kenneth Smith

(57) ABSTRACT

A sequestering subunit comprising an aversive agent and a blocking agent, wherein the blocking agent substantially prevents release of the aversive agent from the sequestering subunit in the gastrointestinal tract for a time period that is greater than 24 hours; a composition comprising a sequestering subunit and a therapeutic agent in releasable form, wherein, optionally, the mechanical fragility of the sequestering subunit is the same as the mechanical fragility of the therapeutic agent in releasable form; a capsule or tablet comprising a sequestering subunit and a therapeutic agent; and a method of preventing abuse of a therapeutic agent.

18 Claims, No Drawings

U.S. PATENT DOCUMENTS

| | | | |
|---|---|---|---|
| 7,658,939 | B2 | 2/2010 | Oshlack et al. |
| 2002/0004509 | A1 | 1/2002 | Palermo et al. |
| 2002/0010127 | A1 | 1/2002 | Oshlack et al. |
| 2002/0013301 | A1 | 1/2002 | Kaiko et al. |
| 2002/0058673 | A1 | 5/2002 | Kaiko et al. |
| 2003/0004177 | A1 | 1/2003 | Kao et al. |
| 2003/0026838 | A1 | 2/2003 | Farrell |
| 2003/0031712 | A1 | 2/2003 | Kaiko et al. |
| 2003/0044458 | A1 | 3/2003 | Wright, IV et al. |
| 2003/0049317 | A1 | 3/2003 | Lindsay |
| 2003/0059397 | A1 | 3/2003 | Hughes |
| 2003/0064099 | A1 | 4/2003 | Oshlack et al. |
| 2003/0064122 | A1 | 4/2003 | Goldberg et al. |
| 2003/0065002 | A1 | 4/2003 | Caruso et al. |
| 2003/0068276 | A1 | 4/2003 | Hughes et al. |
| 2003/0068371 | A1 | 4/2003 | Oshlack et al. |
| 2003/0068375 | A1 | 4/2003 | Wright et al. |
| 2003/0069263 | A1 | 4/2003 | Breder et al. |
| 2003/0073714 | A1 | 4/2003 | Breder et al. |
| 2003/0091635 | A1 | 5/2003 | Baichwal et al. |
| 2003/0118641 | A1 | 6/2003 | Maloney et al. |
| 2003/0124061 | A1 | 7/2003 | Roberts |
| 2003/0124185 | A1 | 7/2003 | Oshlack et al. |
| 2003/0143269 | A1 | 7/2003 | Oshlack et al. |
| 2003/0157168 | A1 | 8/2003 | Breder et al. |
| 2003/0190362 | A1 | 10/2003 | Sackler et al. |
| 2003/0228357 | A1 | 12/2003 | Johnson et al. |
| 2004/0024006 | A1 | 2/2004 | Simon |
| 2004/0086561 | A1 | 5/2004 | Kaiko et al. |
| 2004/0092542 | A1 | 5/2004 | Oshlack et al. |
| 2004/0176402 | A1 | 9/2004 | Oshlack et al. |
| 2004/0186121 | A1 | 9/2004 | Oshlack et al. |
| 2005/0169990 | A1 | 8/2005 | Kao et al. |

FOREIGN PATENT DOCUMENTS

| | | |
|---|---|---|
| EP | 502642 A1 | 9/1992 |
| JP | 59122425 A2 | 7/1984 |
| JP | 10130142 A2 | 5/1998 |

OTHER PUBLICATIONS

MedPage Today, FDA Approves Morphine Naltrexone Combo, John Geer, Aug. 14, 2009.*

Bodmeier, R.; Guo, X. Sarabia, P.F., Skultety, P.F.; "The influence of buffer species and strength on diltiazem HCl release from beads coated with aqueous cationic dispersions": Pharm. Res. vol. 13. pp. 52-56 (1996).

Donbrow, et al. Gradation of microcapsule wall porosity by deposition of polymer mixtures (Eudragit RL and Eudragit RS). Phase Separation of Polymer Mixtures and Effects of External Media and Conditions on Release. J. Microencapsulation, vol. 12, No. 3, pp. 273-285 (1995).

Felton, et al. Influence of Insoluble Excipients on Film Coating Systems. Drug Dev. Ind. Pharmacy; vol. 28, No. 3, pp. 225-243 (2002).

Mendelson et al. Buprenorphine and naloxone interactions in opiate-dependent volunteers. Clin. Pharm. Ther. 60:105-114 (1996).

Rao, et al. Effect of Sodium Lauryl Sulfate on the Release of Rifampicin from Guar Gum Matrix. Indian Journal of Pharmaceutical Science. pp. 404-406 (2000) (Abstract).

Wagner, et al. Influence of chloride ion exchange on the permeabilty and drug release of Eudragit RS 30 D films. J. Cont. Rel. vol. 82, pp. 385-397 (2002).

Weinberg et al. Sublingual absorption of selected opioid analgesics. Clin. Pharmacol. Ther. 44:335-340 (1988).

Weinhold et al. Buprenorphine alone and in combination with naloxone in non-dependent humans. Drug and Alcohol Dependence, 30: 263-274 (1992).

Wells, et al. Effect of Anionic Surfactants on the Release of Chlorpheniramine Maleate From an Inert, Heterogeneous Matrix. Drug Development and Industrial Pharmacy, 18(2): 175-186 (1992).

Knop, K. Influence of buffer solution composition on drug release from pellets coated with neutral and quaternary acrylic polymers and on swelling of free polymer films. Eur. J. Pharm. Sci. vol. 4, pp. 293-300 (1996).

Knop, et al. Influence of surfactants of different charge and concentration on drug release from pellets coated with an aqueous dispersion of quaternary acrylic polymers, S.T.P. Pharma Sci. vol. 6, No. 6, pp. 507-512 (1997).

Rao, et al. Effect of Sodium Lauryl Sulfate on the Release of Rifampicin from Guar Gum Matrix. Indian J. of Pharm. Sci. pp. 404-406 (Sep.-Oct. 2000).

* cited by examiner

SEQUESTERING SUBUNIT AND RELATED COMPOSITIONS AND METHODS

FIELD OF THE INVENTION

This invention pertains to a sequestering subunit comprising an aversive agent and a blocking agent, and related compositions and methods of use, such as in the prevention of abuse of a therapeutic agent.

BACKGROUND OF THE INVENTION

Opioids, also called opioid agonists, are a class of drugs that exhibit opium-like or morphine-like properties. The opioids are employed primarily as moderate to strong analgesics, but have many other pharmacological effects as well, including drowsiness, respiratory depression, changes in mood, and mental clouding without a resulting loss of consciousness. Because of these other pharmacological effects, opioids have become the subject of dependence and abuse. Therefore, a major concern associated with the use of opioids is the diversion of these drugs from the illicit user, e.g., an addict.

Physical dependence may develop upon repeated administrations or extended use of opioids. Physical dependence is gradually manifested after stopping opioid use or is precipitously manifested (e.g., within a few minutes) after administration of a narcotic antagonist (referred to "precipitated withdrawal"). Depending upon the drug upon which dependence has been established and the duration of use and dose, symptoms of withdrawal vary in number and kind, duration and severity. The most common symptoms of the withdrawal syndrome include anorexia, weight loss, pupillary dilation, chills alternating with excessive sweating, abdominal cramps, nausea, vomiting, muscle spasms, hyperirritability, lacrimation, rinorrhea, goose flesh and increased heart rate. Natural abstinence syndromes typically begin to occur 24-48 hours after the last dose, reach maximum intensity about the third day and may not begin to decrease until the third week. Precipitated abstinence syndromes produced by administration of an opioid antagonist vary in intensity and duration with the dose and the specific antagonist, but generally vary from a few minutes to several hours in length.

Psychological dependence or addiction to opioids is characterized by drug-seeking behavior directed toward achieving euphoria and escape from, e.g., psychosocioeconomic pressures. An addict will continue to administer opioids for non-medicinal purposes and in the face of self-harm.

Although opioids, such as morphine, hydromorphone, hydrocodone and oxycodone, are effective in the management of pain, there has been an increase in their abuse by individuals who are psychologically dependent on opioids or who misuse opioids for non-therapeutic reasons. Previous experience with other opioids has demonstrated a decreased abuse potential when opioids are administered in combination with a narcotic antagonist, especially in patients who are ex-addicts (Weinhold et al., *Drug and Alcohol Dependence* 30:263-274 (1992); and Mendelson et al., *Clin. Pharm. Ther.* 60:105-114 (1996)). These combinations, however, do not contain the opioid antagonist that is in a sequestered form. Rather, the opioid antagonist is released in the gastrointestinal system when orally administered and is made available for absorption, relying on the physiology of the host to metabolize differentially the agonist and antagonist and negate the agonist effects.

Previous attempts to control the abuse potential associated with opioid analgesics include, for example, the combination of pentazocine and naloxone in tablets, commercially available in the United States as Talwin®Nx from Sanofi-Winthrop, Canterbury, Australia. Talwin®Nx contains pentazocine hydrochloride equivalent to 50 mg base and naloxone hydrochloride equivalent to 0.5 mg base. Talwin®Nx is indicated for the relief of moderate to severe pain. The amount of naloxone present in this combination has low activity when taken orally, and minimally interferes with the pharmacologic action of pentazocine. However, this amount of naloxone given parenterally has profound antagonistic action to narcotic analgesics. Thus, the inclusion of naloxone is intended to curb a form of misuse of oral pentazocine, which occurs when the dosage form is solubilized and injected. Therefore, this dosage has lower potential for parenteral misuse than previous oral pentazocine formulations. However, it is still subject to patient misuse and abuse by the oral route, for example, by the patient taking multiple doses at once. A fixed combination therapy comprising tilidine (50 mg) and naloxone (4 mg) has been available in Germany for the management of severe pain since 1978 (Valoron®N, Goedecke). The rationale for the combination of these drugs is effective pain relief and the prevention of tilidine addiction through naloxone-induced antagonisms at the tilidine receptors. A fixed combination of buprenorphine and naloxone was introduced in 1991 in New Zealand (Terngesic®Nx, Reckitt & Colman) for the treatment of pain.

International Patent Application No. PCT/US01/04346 (WO 01/58451) to Euroceltique, S.A., describes the use of a pharmaceutical composition that contains a substantially non-releasing opioid antagonist and a releasing opioid agonist as separate subunits that are combined into a pharmaceutical dosage form, e.g., tablet or capsule. However, because the agonist and antagonist are in separate subunits, they can be readily separated. Further, providing the agonist and antagonist as separate subunits, tablets are more difficult to form due to the mechanical sensitivity of some subunits comprising a sequestering agent.

The benefits of the abuse-resistant dosage form are especially great in connection with oral dosage forms of strong opioid agonists (e.g., morphine, hydromorphone, oxycodone or hydrocodone), which provide valuable analgesics but are prone to being abused. This is particularly true for sustained-release opioid agonist products, which have a large dose of a desirable opioid agonist intended to be released over a period of time in each dosage unit. Drug abusers take such sustained release product and crush, grind, extract or otherwise damage the product so that the full contents of the dosage form become available for immediate absorption.

Such abuse-resistant, sustained-release dosage forms have been described in the art (see, for example, U.S. Application Nos. 2003/0124185 and 2003/0044458). However, it is believed that substantial amounts of the opioid antagonist or other aversive agent found in these sequestered forms are released over time (usually less than 24 hours) due to the osmotic pressure that builds up in the core of the sequestered form, as water permeates through the sequestered form into the core. The high osmotic pressure inside the core of the sequestered form causes the opioid antagonist or aversive agent to be pushed out of the sequestered form, thereby causing the opioid antagonist or aversive agent to be released from the sequestered form.

In view of the foregoing drawbacks of the sequestered forms of the prior art, there exists a need in the art for a sequestered form of an opioid antagonist or other aversive agent that is not substantially released from the sequestered form due to osmotic pressure. The invention provides such a sequestering form of an opioid antagonist or aversive agent.

This and other objects and advantages of the invention, as well as additional inventive features, will be apparent from the description of the invention provided herein.

BRIEF SUMMARY OF THE INVENTION

The invention provides a sequestering subunit comprising an aversive agent and a blocking agent, wherein the blocking agent substantially prevents release of the aversive agent from the sequestering subunit in the gastrointestinal tract for a time period that is greater than 24 hours.

Also provided by the invention is a composition comprising a sequestering subunit of the invention and a therapeutic agent in releasable form. Optionally, the mechanical fragility of the sequestering subunit is the same as the mechanical fragility of the therapeutic agent in releasable form.

The invention also provides a capsule suitable for oral administration comprising a plurality of composite subunits, wherein each composite subunit comprises the sequestering subunit coated with a therapeutic agent in releasable form. A capsule suitable for oral administration comprising a plurality of sequestering subunits of the invention and a plurality of therapeutic subunits, each of which comprises a therapeutic agent in releasable form is further provided.

Further provided is a tablet suitable for oral administration comprising a first layer comprising a sequestering subunit of the invention and a second layer comprising a therapeutic agent in releasable form, wherein the first layer is coated with the second layer. The invention also provides a tablet suitable for oral administration comprising a single layer comprising a therapeutic agent in releasable form and a plurality of the sequestering subunits of the invention dispersed throughout the layer.

The invention further provides a method of preventing abuse of a therapeutic agent, which method comprises incorporating the therapeutic agent in any composition of the invention.

DETAILED DESCRIPTION OF THE INVENTION

The invention provides a sequestering subunit comprising an aversive agent and a blocking agent, wherein the blocking agent substantially prevents release of the aversive agent from the sequestering subunit in the gastrointestinal tract for a time period that is greater than 24 hours.

With respect to the invention, the term "sequestering subunit" as used herein refers to any means for containing an aversive agent and preventing or substantially preventing the release thereof in the gastrointestinal tract when intact, i.e., when not tampered with. The term "blocking agent" as used herein refers to the means by which the sequestering subunit is able to prevent substantially the aversive agent from being released.

The terms "substantially prevents," "prevents," or any words stemming therefrom, as used herein, means that the aversive agent is substantially not released from the sequestering subunit in the gastrointestinal tract. By "substantially not released" is meant that the aversive agent may be released in a small amount, but the amount released does not affect or does not significantly affect the analgesic efficacy when the dosage form is orally administered to a host, e.g., a mammal (e.g., a human), as intended. The terms "substantially prevents," "prevents," or any words stemming therefrom, as used herein, does not necessarily imply a complete or 100% prevention. Rather, there are varying degrees of prevention of which one of ordinary skill in the art recognizes as having a potential benefit. In this regard, the blocking agent substantially prevents or prevents the release of the aversive agent to the extent that at least about 80% of the aversive agent is prevented from being released from the sequestering subunit in the gastrointestinal tract for a time period that is greater than 24 hours. Preferably, the blocking agent prevents release of at least about 90% of the aversive agent from the sequestering subunit in the gastrointestinal tract for a time period that is greater than 24 hours. More preferably, the blocking agent prevents release of at least about 95% of the aversive agent from the sequestering subunit. Most preferably, the blocking agent prevents release of at least about 99% of the aversive agent from the sequestering subunit in the gastrointestinal tract for a time period that is greater than 24 hours.

The blocking agent prevents or substantially prevents the release of the aversive agent in the gastrointestinal tract for a time period that is greater than 24 hours, e.g., between 24 and 25 hours, 30 hours, 35 hours, 40 hours, 45 hours, 48 hours, 50 hours, 55 hours, 60 hours, 65 hours, 70 hours, 72 hours, 75 hours, 80 hours, 85 hours, 90 hours, 95 hours, or 100 hours; etc. Preferably, the time period for which the release of the aversive agent is prevented or substantially prevented in the gastrointestinal tract is at least about 48 hours. More preferably, the blocking agent prevents or substantially prevents the release for a time period of at least about 72 hours.

For purposes of this invention, the amount of the aversive agent released after oral administration can be measured in-vitro by dissolution testing as described in the United States Pharmacopeia (USP26) in chapter <711> Dissolution. For example, using 900 mL of 0.1 N HCl, Apparatus 2 (Paddle), 75 rpm, at 37° C. to measure release at various times from the dosage unit. Other methods of measuring the release of an aversive agent from a sequestering subunit over a given period of time are known in the art. See, e.g., USP26 and Examples 1 and 2 below.

Without being bound to any particular theory, it is believed that the sequestering subunit of the invention overcomes the limitations of the sequestered forms of an aversive agent known in the art in that the sequestering subunit of the invention reduces osmotically-driven release of the aversive agent from the sequestering subunit. Furthermore, it is believed that the present inventive sequestering subunit reduces the release of the aversive agent for a longer period of time (e.g., greater than 24 hours) in comparison to the sequestered forms of aversive agents known in the art. The fact that the sequestered subunit of the invention provides a longer prevention of release of the aversive agent is particularly relevant, since precipitated withdrawal could occur after the time for which the therapeutic agent is released and acts. It is well known that the gastrointestinal tract transit time for individuals varies greatly within the population. Hence, the residue of the dosage form may be retained in the tract for longer than 24 hours, and in some cases for longer than 48 hours. It is further well known that opioid analgesics cause decreased bowel motility, further prolonging gastrointestinal tract transit time. Currently, sustained-release forms having an effect over a 24 hour time period have been approved by the Food and Drug Administration. In this regard, the present inventive sequestering subunit provides prevention of release of the aversive agent for a time period that is greater than 24 hours when the sequestering subunit has not been tampered.

The sequestering subunit of the invention is designed to prevent substantially the release of the aversive agent when intact. By "intact" is meant that a dosage form has not undergone tampering. The term "tampering" is meant to include any manipulation by mechanical, thermal and/or chemical means, which changes the physical properties of the dosage form. The tampering can be, for example, crushing, shearing, grinding, chewing, dissolution in a solvent, heating (for example, greater than about 45° C.), or any combination thereof. When the sequestering subunit of the invention has been tampered with, the aversive agent is immediately released from the sequestering subunit.

By "subunit" is meant to include a composition, mixture, particle; etc., that can provide a dosage form (e.g., an oral dosage form) when combined with another subunit. The subunit can be in the form of a bead, pellet, granule, spheroid, or the like, and can be combined with additional same or different subunits, in the form of a capsule, tablet or the like, to provide a dosage form, e.g., an oral dosage form.

The blocking agent of the present inventive sequestering subunit can be a system comprising a first aversive agent-impermeable material and a core. By "aversive agent-impermeable material" is meant any material that is substantially impermeable to the aversive agent, such that the aversive agent is substantially not released from the sequestering subunit. The term "substantially impermeable" as used herein does not necessarily imply complete or 100% impermeability. Rather, there are varying degrees of impermeability of which one of ordinary skill in the art recognizes as having a potential benefit. In this regard, the aversive agent-impermeable material substantially prevents or prevents the release of the aversive agent to an extent that at least about 80% of the aversive agent is prevented from being released from the sequestering subunit in the gastrointestinal tract for a time period that is greater than 24 hours. Preferably, the aversive agent-impermeable material prevents release of at least about 90% of the aversive agent from the sequestering subunit in the gastrointestinal tract for a time period that is greater than 24 hours. More preferably, the aversive agent-impermeable material prevents release of at least about 95% of the aversive agent from the sequestering subunit. Most preferably, the aversive agent-impermeable material prevents release of at least about 99% of the aversive agent from the sequestering subunit in the gastrointestinal tract for a time period that is greater than 24 hours. The aversive agent-impermeable material prevents or substantially prevents the release of the aversive agent in the gastrointestinal tract for a time period that is greater than 24 hours, and desirably, at least about 48 hours. More desirably, the aversive agent-impermeable material prevents or substantially prevents the release of the adversive agent from the sequestering subunit for a time period of at least about 72 hours.

Preferably, the first aversive agent-impermeable material comprises a hydrophobic material, such that the antagonist is not released or substantially not released during its transit through the gastrointestinal tract when administered orally as intended, without having been tampered with. Suitable hydrophobic materials for use in the invention are described herein and set forth below. The hydrophobic material is preferably a pharmaceutically acceptable hydrophobic material. Preferably, the pharmaceutically acceptable hydrophobic material comprises a cellulose polymer.

It is preferred that the first aversive agent-impermeable material comprises a polymer insoluble in the gastrointestinal tract. One of ordinary skill in the art appreciates that a polymer that is insoluble in the gastrointestinal tract will prevent the release of the aversive agent upon ingestion of the sequestering subunit. The polymer can be a cellulose or an acrylic polymer. Desirably, the cellulose is selected from the group consisting of ethylcellulose, cellulose acetate, cellulose propionate, cellulose acetate propionate, cellulose acetate butyrate, cellulose acetate phthalate, cellulose triacetate, and combinations thereof. Ethylcellulose includes, for example, one that has an ethoxy content of about 44 to about 55%. Ethylcellulose can be used in the form of an aqueous dispersion, an alcoholic solution, or a solution in other suitable solvents. The cellulose can have a degree of substitution (D.S.) on the anhydroglucose unit, from greater than zero and up to 3 inclusive. By "degree of substitution" is meant the average number of hydroxyl groups on the anhydroglucose unit of the cellulose polymer that are replaced by a substituting group. Representative materials include a polymer selected from the group consisting of cellulose acylate, cellulose diacylate, cellulose triacylate, cellulose acetate, cellulose diacetate, cellulose triacetate, monocellulose alkanylate, dicellulose alkanylate, tricellulose alkanylate, monocellulose alkenylates, dicellulose alkenylates, tricellulose alkenylates, monocellulose aroylates, dicellulose aroylates, and tricellulose aroylates.

More specific celluloses include cellulose propionate having a D.S. of 1.8 and a propyl content of 39.2 to 45 and a hydroxy content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxy content of 0.5 to 4.7%; cellulose triacylate having a D.S. of 2.9 to 3, such as cellulose triacetate, cellulose trivalerate, cellulose trilaurate, cellulose tripatmitate, cellulose trisuccinate, and cellulose trioctanoate; cellulose diacylates having a D.S. of 2.2 to 2.6, such as cellulose disuccinate, cellulose dipalmitate, cellulose dioctanoate, cellulose dipentanoate, and coesters of cellulose, such as cellulose acetate butyrate, cellulose acetate octanoate butyrate, and cellulose acetate propionate.

Additional cellulose polymers useful for preparing a sequestering subunit of the invention includes acetaldehyde dimethyl cellulose acetate, cellulose acetate ethylcarbamate, cellulose acetate methycarbamate, and cellulose acetate dimethylaminocellulose acetate.

The acrylic polymer preferably is selected from the group consisting of methacrylic polymers, acrylic acid and methacrylic acid copolymers, methyl methacrylate copolymers, ethoxyethyl methacrylates, cyanoethyl methacrylate, poly (acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly (methacrylic acid anhydride), glycidyl methacrylate copolymers, and combinations thereof. An acrylic polymer useful for preparation of a sequestering subunit of the invention includes acrylic resins comprising copolymers synthesized from acrylic and methacrylic acid esters (e.g., the copolymer of acrylic acid lower alkyl ester and methacrylic acid lower alkyl ester) containing about 0.02 to about 0.03 mole of a tri (lower alkyl) ammonium group per mole of the acrylic and methacrylic monomer used. An example of a suitable acrylic resin is ammonio methacrylate copolymer NF21, a polymer manufactured by Rohm Pharma GmbH, Darmstadt, Germany, and sold under the Eudragit® trademark. Eudragit RS30D is preferred. Eudragit® is a water-insoluble copolymer of ethyl acrylate (EA), methyl methacrylate (MM) and trimethylammoniumethyl methacrylate chloride (TAM) in which the molar ratio of TAM to the remaining components (EA and MM) is 1:40. Acrylic resins, such as Eudragit®, can be used in the form of an aqueous dispersion or as a solution in suitable solvents.

In another preferred embodiment, the aversive agent-impermeable material is selected from the group consisting of polylactic acid, polyglycolic acid, a co-polymer of polylactic acid and polyglycolic acid, and combinations thereof. In certain other embodiments, the hydrophobic material includes a biodegradable polymer comprising a poly(lactic/glycolic acid) ("PLGA"), a polylactide, a polyglycolide, a polyanhydride, a polyorthoester, polycaprolactones, polyphosphazenes, polysaccharides, proteinaceous polymers, polyesters, polydioxanone, polygluconate, polylactic-acid-polyethylene oxide copolymers, poly(hydroxybutyrate), polyphosphoester or combinations thereof.

Preferably, the biodegradable polymer comprises a poly (lactic/glycolic acid), a copolymer of lactic and glycolic acid, having a molecular weight of about 2,000 to about 500,000 daltons. The ratio of lactic acid to glycolic acid is preferably from about 100:1 to about 25:75, with the ratio of lactic acid to glycolic acid of about 65:35 being more preferred.

Poly(lactic/glycolic acid) can be prepared by the procedures set forth in U.S. Pat. No. 4,293,539 (Ludwig et al.), which is incorporated herein by reference. In brief, Ludwig prepares the copolymer by condensation of lactic acid and glycolic acid in the presence of a readily removable polymerization catalyst (e.g., a strong ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction can be conducted without solvents at a temperature from about 100° C. to about 250° C. for about 48 to about 96 hours, preferably under a reduced pressure to facilitate removal of water and by-products. Poly(lactic/glycolic acid) is then recovered by filtering the molten reaction mixture in an organic solvent, such as dichloromethane or acetone, and then filtering to remove the catalyst.

Suitable plasticizers, for example, acetyl triethyl citrate, acetyl tributyl citrate, triethyl citrate, diethyl phthalate, dibutyl phthalate, or dibutyl sebacate, also can be admixed with the polymer used to make the sequestering subunit. Additives, such as coloring agents, talc and/or magnesium stearate, and other additives also can be used in making the present inventive sequestering subunit.

When the blocking agent is a system comprising a first aversive agent-impermeable material and a core, the sequestering subunit can be in one of several different forms. For example, the system can further comprise a second aversive agent-impermeable material, in which case the sequestering unit comprises an aversive agent, a first aversive agent-impermeable material, a second aversive agent-impermeable material, and a core. In this instance, the core is coated with the first aversive agent-impermeable material, which, in turn, is coated with the aversive agent, which, in turn, is coated with the second aversive agent-impermeable material. The first aversive agent-impermeable material and second aversive agent-impermeable material substantially prevent release of the aversive agent from the sequestering subunit in the gastrointestinal tract for a time period that is greater than 24 hours. In some instances, it is preferable that the first aversive agent-impermeable material is the same as the second aversive agent-impermeable material. In other instances, the first aversive agent-impermeable material is different from the second aversive agent-impermeable material. It is within the skill of the ordinary artisan to determine whether or not the first and second aversive agent-impermeable materials should be the same or different. Factors that influence the decision as to whether the first and second aversive agent-impermeable materials should be the same or different can include whether a layer to be placed over the aversive agent-impermeable material requires certain properties to prevent dissolving part or all of the aversive agent-impermeable layer when applying the next layer or properties to promote adhesion of a layer to be applied over the aversive agent-impermeable layer.

Alternatively, the aversive agent can be incorporated into the core, and the core is coated with the first aversive agent-impermeable material. In this case, the invention provides a sequestering subunit comprising an aversive agent, a core and a first aversive agent-impermeable material, wherein the aversive agent is incorporated into the core and the core is coated with the first aversive agent-impermeable material, and wherein the first aversive agent-impermeable material substantially prevents release of the aversive agent from the sequestering subunit in the gastrointestinal tract for a time period that is greater than 24 hours. By "incorporate" and words stemming therefrom, as used herein is meant to include any means of incorporation, e.g., homogeneous dispersion of the aversive agent throughout the core, a single layer of the aversive agent coated on top of a core, or a multi-layer system of the aversive agent, which comprises the core.

In another alternative embodiment, the core comprises a water-insoluble material, and the core is coated with the aversive agent, which, in turn, is coated with the first aversive agent-impermeable material. In this case, the invention further provides a sequestering subunit comprising an aversive agent, a first aversive agent-impermeable material, and a core, which comprises a water-insoluble material, wherein the core is coated with the aversive agent, which, in turn, is coated with the first aversive agent-impermeable material, and wherein the first aversive agent-impermeable material substantially prevents release of the aversive agent from the sequestering subunit in the gastrointestinal tract for a time period that is greater than 24 hours. The term "water-insoluble material" as used herein means any material that is substantially water-insoluble. The term "substantially water-insoluble" does not necessarily refer to complete or 100% water-insolubility. Rather, there are varying degrees of water insolubility of which one of ordinary skill in the art recognizes as having a potential benefit. Preferred water-insoluble materials include, for example, microcrystalline cellulose, a calcium salt, and a wax. Calcium salts include, but are not limited to, a calcium phosphate (e.g., hydroxyapatite, apatite; etc.), calcium carbonate, calcium sulfate, calcium stearate, and the like. Waxes include, for example, carnuba wax, beeswax, petroleum wax, candelilla wax, and the like.

For purposes of the invention, the aversive agent can be any agent that negates the effect of the therapeutic agent or produces an unpleasant or punishing stimulus or effect, which will deter or cause avoidance of tampering with the sequestering subunit or compositions comprising the same. Desirably, the aversive agent does not harm a host by its administration or consumption but has properties that deter its administration or consumption, e.g., by chewing and swallowing or by crushing and snorting, for example. The aversive agent can have a strong or foul taste or smell, provide a burning or tingling sensation, cause a lachrymation response, nausea, vomiting, or any other unpleasant or repugnant sensation, or color tissue, for example. Preferably, the aversive agent is selected from the group consisting of an antagonist of a therapeutic agent, a bittering agent, a dye, a gelling agent, and an irritant. Exemplary aversive agents include capsaicin, dye, bittering agents and emetics.

By "antagonist of a therapeutic agent" is meant any drug or molecule, naturally-occurring or synthetic, that binds to the same target molecule (e.g., a receptor) of the therapeutic agent, yet does not produce a therapeutic, intracellular, or in vivo response. In this regard, the antagonist of a therapeutic agent binds to the receptor of the therapeutic agent, thereby preventing the therapeutic agent from acting on the receptor, thereby preventing the achievement of a "high" in the host.

The therapeutic agent can be any medicament. Preferably, the therapeutic agent is one that is addictive (physically and/or psychologically) and typically leads to abuse. In this regard, the therapeutic agent can be an opioid agonist. By "opioid" is meant to include a drug, hormone, or other chemical or biological substance, natural or synthetic, having a sedative, narcotic, or otherwise similar effect(s) to those containing opium or its natural or synthetic derivatives. By "opioid agonist," sometimes used herein interchangeably with terms "opioid" and "opioid analgesic," is meant to include one or more opioid agonists, either alone or in combination, and is further meant to include the base of the opioid, mixed or combined agonist-antagonists, partial agonists, pharmaceutically acceptable salts thereof, stereoisomers thereof, ethers thereof, esters thereof, and combinations thereof.

The pharmaceutically acceptable salts of an opioid agonist include metal salts, such as sodium salt, potassium salt, cesium salt, and the like; alkaline earth metals, such as calcium salt, magnesium salt, and the like; organic amine salts, such as triethylamine salt, pyridine salt, picoline salt, ethanolamine salt, triethanolamine salt, dicyclohexylamine salt, N,N'-dibenzylethylenediamine salt, and the like; inorganic acid salts, such as hydrochloride, hydrobromide, sulfate, phosphate, and the like; organic acid salts, such as formate, acetate, trifluoroacetate, maleate, tartrate, and the like; sulfonates, such as methanesulfonate, benzenesulfonate, p-toluenesulfonate, and the like; amino acid salts, such as arginate, asparginate, glutamate, and the like.

Opioid agonists include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydroetorphine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenazocine, phenomorphan, phenoperidine, piminodine, piritramide, propheptazine, promedol, properidine, propiram, propoxyphene, sufentanil, tramadol, tilidine, derivatives or complexes thereof, pharmaceutically acceptable salts thereof, and combinations thereof. Preferably, the opioid agonist is selected from the group consisting of hydrocodone, hydromorphone, oxycodone, dihydrocodeine, codeine, dihydromorphine, morphine, buprenorphine, derivatives or complexes thereof, pharmaceutically acceptable salts thereof, and combinations thereof. Most preferably, the opioid agonist is morphine, hydromorphone, oxycodone or hydrocodone. In a preferred embodiment, the opioid agonist comprises oxycodone or hydrocodone and is present in the dosage form in an amount of about 15 to about 45 mg, and the opioid antagonist comprises naltrexone and is present in the dosage form in an amount of about 0.5 to about 5 mg.

Equianalgesic doses of these opioids, in comparison to a 15 mg dose of hydrocodone, are set forth in Table 1 below:

TABLE 1

Equianalgesic Doses of Opioids

| Opioid | Calculated Dose (mg) |
|---|---|
| Oxycodone | 13.5 |
| Codeine | 90.0 |
| Hydrocodone | 15.0 |
| Hydromorphone | 3.375 |
| Levorphanol | 1.8 |
| Meperidine | 135.0 |
| Methadone | 9.0 |
| Morphine | 27.0 |

Hydrocodone is a semisynthetic narcotic analgesic and antitussive with multiple nervous system and gastrointestinal actions. Chemically, hydrocodone is 4,5-epoxy-3-methoxy-17-methylmorphinan-6-one, and is also known as dihydrocodeinone. Like other opioids, hydrocodone can be habit-forming and can produce drug dependence of the morphine type. Like other opium derivatives, excess doses of hydrocodone will depress respiration.

Oral hydrocodone is also available in Europe (e.g., Belgium, Germany, Greece, Italy, Luxembourg, Norway and Switzerland) as an antitussive agent. A parenteral formulation is also available in Germany as an antitussive agent. For use as an analgesic, hydrocodone bitartrate is commonly available in the United States only as a fixed combination with non-opiate drugs (e.g., ibuprofen, acetaminophen, aspirin; etc.) for relief of moderate to moderately severe pain.

A common dosage form of hydrocodone is in combination with acetaminophen and is commercially available, for example, as Lortab® in the United States from UCB Pharma, Inc. (Brussels, Belgium), as 2.5/500 mg, 5/500 mg, 7.5/500 mg and 10/500 mg hydrocodone/acetaminophen tablets. Tablets are also available in the ratio of 7.5 mg hydrocodone bitartrate and 650 mg acetaminophen and a 7.5 mg hydrocodone bitartrate and 750 mg acetaminophen. Hydrocodone, in combination with aspirin, is given in an oral dosage form to adults generally in 1-2 tablets every 4-6 hours as needed to alleviate pain. The tablet form is 5 mg hydrocodone bitartrate and 224 mg aspirin with 32 mg caffeine; or 5 mg hydrocodone bitartrate and 500 mg aspirin. Another formulation comprises hydrocodone bitartrate and ibuprofen. Vicoprofen®, commercially available in the U.S. from Knoll Laboratories (Mount Olive, N.J.), is a tablet containing 7.5 mg hydrocodone bitartrate and 200 mg ibuprofen. The invention is contemplated to encompass all such formulations, with the inclusion of the opioid antagonist and/or aversive agent in sequestered form as part of a subunit comprising an opioid agonist.

Oxycodone, chemically known as 4,5-epoxy-14-hydroxy-3-methoxy-17-methylmorphinan-6-one, is an opioid agonist whose principal therapeutic action is analgesia. Other therapeutic effects of oxycodone include anxiolysis, euphoria and feelings of relaxation. The precise mechanism of its analgesic action is not known, but specific CNS opioid receptors for endogenous compounds with opioid-like activity have been identified throughout the brain and spinal cord and play a role in the analgesic effects of this drug.

Oxycodone is commercially available in the United States, e.g., as Oxycotin® from Purdue Pharma L.P. (Stamford, Conn.), as controlled-release tablets for oral administration containing 10 mg, 20 mg, 40 mg or 80 mg oxycodone hydrochloride, and as OxyIR™, also from Purdue Pharma L.P., as immediate-release capsules containing 5 mg oxycodone hydrochloride. The invention is contemplated to encompass all such formulations, with the inclusion of an opioid antagonist and/or aversive agent in sequestered form as part of a subunit comprising an opioid agonist.

Oral hydromorphone is commercially available in the United States, e.g., as Dilaudid® from Abbott Laboratories (Chicago, Ill.).

Oral morphine is commercially available in the United States, e.g., as Kadian® from Faulding Laboratories (Piscataway, N.J.).

In embodiments in which the opioid agonist comprises hydrocodone, the sustained-release oral dosage forms can include analgesic doses from about 8 mg to about 50 mg of hydrocodone per dosage unit. In sustained-release oral dosage forms where hydromorphone is the therapeutically active opioid, it is included in an amount from about 2 mg to about 64 mg hydromorphone hydrochloride. In another embodiment, the opioid agonist comprises morphine, and the sustained-release oral dosage forms of the invention include from about 2.5 mg to about 800 mg morphine, by weight. In yet another embodiment, the opioid agonist comprises oxycodone and the sustained-release oral dosage forms include from about 2.5 mg to about 800 mg oxycodone. In certain preferred embodiments, the sustained-release oral dosage forms include from about 20 mg to about 30 mg oxycodone. Controlled release oxycodone formulations are known in the art. The following documents describe various controlled-release oxycodone formulations suitable for use in the invention described herein, and processes for their manufacture: U.S. Pat. Nos. 5,266,331; 5,549,912; 5,508,042; and 5,656,295, which are incorporated herein by reference. The opioid agonist can comprise tramadol and the sustained-release oral dosage forms can include from about 25 mg to 800 mg tramadol per dosage unit.

In the instance when the therapeutic agent is an opioid agonist, the aversive agent preferably is an opioid antagonist, such as naltrexone, naloxone, nalmefene, cyclazacine, levallorphan, derivatives or complexes thereof, pharmaceutically acceptable salts thereof, and combinations thereof. More preferably, the opioid antagonist is naloxone or naltrexone. By "opioid antagonist" is meant to include one or more opioid antagonists, either alone or in combination, and is further meant to include partial antagonists, pharmaceutically acceptable salts thereof, stereoisomers thereof, ethers thereof, esters thereof, and combinations thereof. The pharmaceutically acceptable salts include metal salts, such as sodium salt, potassium salt, cesium salt, and the like; alkaline earth metals, such as calcium salt, magnesium salt, and the like; organic amine salts, such as triethylamine salt, pyridine salt, picoline salt, ethanolamine salt, triethanolamine salt, dicyclohexylamine salt, N,N-dibenzylethylenediamine salt, and the like; inorganic acid salts, such as hydrochloride, hydrobromide, sulfate, phosphate, and the like; organic acid salts, such as formate, acetate, trifluoroacetate, maleate, tartrate, and the like; sulfonates, such as methanesulfonate, benzenesulfonate, p-toluenesulfonate, and the like; amino acid salts, such as arginate, asparginate, glutamate, and the like. In certain embodiments, the amount of the opioid antagonist, present in sequestered form, can be about 10 ng to about 275 mg. In a preferred embodiment, when the antagonist is naltrexone, it is preferable that the intact dosage form releases less than 0.125 mg or less within 24 hours, with 0.25 mg or greater of naltrexone released after 1 hour when the dosage form is crushed or chewed.

In a preferred embodiment, the opioid antagonist comprises naloxone. Naloxone is an opioid antagonist, which is almost void of agonist effects. Subcutaneous doses of up to 12 mg of naloxone produce no discernable subjective effects, and 24 mg naloxone causes only slight drowsiness. Small doses (0.4-0.8 mg) of naloxone given intramuscularly or intravenously in man prevent or promptly reverse the effects of morphine-like opioid agonist. One mg of naloxone intravenously has been reported to block completely the effect of 25 mg of heroin. The effects of naloxone are seen almost immediately after intravenous administration. The drug is absorbed after oral administration, but has been reported to be metabolized into an inactive form rapidly in its first passage through the liver, such that it has been reported to have significantly lower potency than when parenterally administered. Oral dosages of more than 1 g have been reported to be almost completely metabolized in less than 24 hours. It has been reported that 25% of naloxone administered sublingually is absorbed (Weinberg et al., *Clin. Pharmacol. Ther.* 44:335-340 (1988)).

In another preferred embodiment, the opioid antagonist comprises naltrexone. In the treatment of patients previously addicted to opioids, naltrexone has been used in large oral doses (over 100 mg) to prevent euphorigenic effects of opioid agonists. Naltrexone has been reported to exert strong preferential blocking action against mu over delta sites. Naltrexone is known as a synthetic congener of oxymorphone with no opioid agonist properties, and differs in structure from oxymorphone by the replacement of the methyl group located on the nitrogen atom of oxymorphone with a cyclopropylmethyl group. The hydrochloride salt of naltrexone is soluble in water up to about 100 mg/cc. The pharmacological and pharmacokinetic properties of naltrexone have been evaluated in multiple animal and clinical studies. See, e.g., Gonzalez et al. *Drugs* 35:192-213 (1988). Following oral administration, naltrexone is rapidly absorbed (within 1 hour) and has an oral bioavailability ranging from 5-40%. Naltrexone's protein binding is approximately 21% and the volume of distribution following single-dose administration is 16.1 L/kg.

Naltrexone is commercially available in tablet form (Revia®, DuPont (Wilmington, Del.)) for the treatment of alcohol dependence and for the blockade of exogenously administered opioids. See, e.g., Revia (naltrexone hydrochloride tablets), Physician's Desk Reference, 51$^{st}$ ed., Montvale, N.J.; and *Medical Economics* 51:957-959 (1997). A dosage of 50 mg Revia® blocks the pharmacological effects of 25 mg IV administered heroin for up to 24 hours. It is known that, when coadministered with morphine, heroin or other opioids on a chronic basis, naltrexone blocks the development of physical dependence to opioids. It is believed that the method by which naltrexone blocks the effects of heroin is by competitively binding at the opioid receptors. Naltrexone has been used to treat narcotic addiction by complete blockade of the effects of opioids. It has been found that the most successful use of naltrexone for a narcotic addiction is with narcotic addicts having good prognosis, as part of a comprehensive occupational or rehabilitative program involving behavioral control or other compliance-enhancing methods. For treatment of narcotic dependence with naltrexone, it is desirable that the patient be opioid-free for at least 7-10 days. The initial dosage of naltrexone for such purposes has typically been about 25 mg, and if no withdrawal signs occur, the dosage may be increased to 50 mg per day. A daily dosage of 50 mg is considered to produce adequate clinical blockade of the actions of parenterally administered opioids. Naltrexone also has been used for the treatment of alcoholism as an adjunct with social and psychotherapeutic methods.

Other preferred opioid antagonists include, for example, cyclazocine and naltrexone, both of which have cyclopropylmethyl substitutions on the nitrogen, retain much of their efficacy by the oral route, and last longer, with durations approaching 24 hours after oral administration.

The aversive agent of the present inventive sequestering subunit can be a bittering agent. The term "bittering agent" as used herein refers to any agent that provides an unpleasant taste to the host upon inhalation and/or swallowing of a tampered dosage form comprising the sequestering subunit. With the inclusion of a bittering agent in the sequestering subunit, the intake of the tampered dosage form produces a bitter taste upon inhalation or oral administration, which, in certain embodiments, spoils or hinders the pleasure of obtaining a high from the tampered dosage form, and preferably prevents the abuse of the dosage form.

Various bittering agents can be employed including, for example, and without limitation, natural, artificial and synthetic flavor oils and flavoring aromatics and/or oils, oleoresins and extracts derived from plants, leaves, flowers, fruits, and so forth, and combinations thereof. Nonlimiting representative flavor oils include spearmint oil, peppermint oil, eucalyptus oil, oil of nutmeg, allspice, mace, oil of bitter almonds, menthol and the like. Also useful bittering agents are artificial, natural and synthetic fruit flavors such as citrus oils, including lemon, orange, lime, and grapefruit, fruit essences, and so forth. Additional bittering agents include sucrose derivatives (e.g., sucrose octaacetate), chlorosucrose derivatives, quinine sulphate, and the like. A preferred bittering agent for use in the invention is Denatonium Benzoate NF-Anhydrous, sold under the name Bitrex™ (Macfarlan Smith Limited, Edinburgh, UK).

A bittering agent can be added to the formulation in an amount of less than about 50% by weight, preferably less than about 10% by weight, more preferably less than about 5% by weight of the dosage form, and most preferably in an amount ranging from about 0.1 to 1.0 percent by weight of the dosage form, depending on the particular bittering agent(s) used.

Alternatively, the aversive agent of the present inventive sequestering subunit can be a dye. The term "dye" as used herein refers to any agent that causes discoloration of the tissue in contact. In this regard, if the sequestering subunit is tampered with and the contents are snorted, the dye will discolor the nasal tissues and surrounding tissues thereof. Preferred dyes are those that can bind strongly with subcutaneous tissue proteins and are well-known in the art. Dyes useful in applications ranging from, for example, food coloring to tattooing, are exemplary dyes suitable for the invention. Food coloring dyes include, but are not limited to FD&C Green #3 and FD&C Blue #1, as well as any other FD&C or D&C color. Such food dyes are commercially available through companies, such as Voigt Global Distribution (Kansas City, Mo.).

Alternatively, the aversive agent of the present inventive sequestering subunit can be a gelling agent. The term "gelling agent" as used herein refers to any agent that provides a gel-like quality to the tampered dosage form, which slows the absorption of the therapeutic agent, which is formulated with the sequestering subunit, such that a host is less likely to obtain a rapid "high." In certain preferred embodiments, when the dosage form is tampered with and exposed to a small amount (e.g., less than about 10 ml) of an aqueous liquid (e.g., water), the dosage form will be unsuitable for injection and/or inhalation. Upon the addition of the aqueous liquid, the tampered dosage form preferably becomes thick and viscous, rendering it unsuitable for injection. The term "unsuitable for injection" is defined for purposes of the invention to mean that one would have substantial difficulty injecting the dosage form (e.g., due to pain upon administration or difficulty pushing the dosage form through a syringe) due to the viscosity imparted on the dosage form, thereby reducing the potential for abuse of the therapeutic agent in the dosage form. In certain embodiments, the gelling agent is present in such an amount in the dosage form that attempts at evaporation (by the application of heat) to an aqueous mixture of the dosage form in an effort to produce a higher concentration of the therapeutic agent, produces a highly viscous substance unsuitable for injection. When nasally inhaling the tampered dosage form, the gelling agent can become gel-like upon administration to the nasal passages, due to the moisture of the mucous membranes. This also makes such formulations aversive to nasal administration, as the gel will stick to the nasal passage and minimize absorption of the abusable substance.

Various gelling agents can be employed in the sequestering subunit of the invention, including, for example, and without limitation, sugars or sugar-derived alcohols, such as mannitol, sorbitol, and the like, starch and starch derivatives, cellulose derivatives, such as microcrystalline cellulose, sodium carboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacant, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof; etc. In certain preferred embodiments, the gelling agent is xanthan gum. In other preferred embodiments, the gelling agent of the invention is pectin. The pectin or pectic substances useful for this invention include not only purified or isolated pectates but also crude natural pectin sources, such as apple, citrus or sugar beet residues, which have been subjected, when necessary, to esterification or de-esterification, e.g., by alkali or enzymes. Preferably, the pectins used in this invention are derived from citrus fruits, such as lime, lemon, grapefruit, and orange.

With the inclusion of a gelling agent in the dosage form, the gelling agent preferably imparts a gel-like quality to the dosage form upon tampering that spoils or hinders the pleasure of obtaining a rapid high from due to the gel-like consistency of the tampered dosage form in contact with the mucous membrane, and in certain embodiments, prevents the abuse of the dosage form by minimizing absorption, e.g., in the nasal passages. A gelling agent can be added to the formulation in a ratio of gelling agent to opioid agonist of from about 1:40 to about 40:1 by weight, preferably from about 1:1 to about 30:1 by weight, and more preferably from about 2:1 to about 10:1 by weight of the opioid agonist. In certain other embodiments, the dosage form forms a viscous gel having a viscosity of at least about 10 cP after the dosage form is tampered with by dissolution in an aqueous liquid (from about 0.5 to about 10 ml and preferably from 1 to about 5 ml). Most preferably, the resulting mixture will have a viscosity of at least about 60 cP.

The aversive agent of the present inventive sequestering subunit can alternatively be an irritant. The term "irritant" as used herein includes a compound used to impart an irritating, e.g., burning or uncomfortable, sensation to an abuser administering a tampered dosage form of the invention. Use of an irritant will discourage an abuser from tampering with the dosage form and thereafter inhaling, injecting, or swallowing the tampered dosage form. Preferably, the irritant is released when the dosage form is tampered with and provides a burning or irritating effect to the abuser upon inhalation, injection, and/or swallowing the tampered dosage form.

Various irritants can be employed including, for example, and without limitation, capsaicin, a capsaicin analog with similar type properties as capsaicin, and the like. Some capsaicin analogues or derivatives include, for example, and without limitation, resiniferatoxin, tinyatoxin, heptanoylisobutylamide, heptanoyl guaiacylamide, other isobutylamides or guaiacylamides, dihydrocapsaicin, homovanillyl octylester, nonanoyl vanillylamide, or other compounds of the class known as vanilloids. Resiniferatoxin is described, for example, in U.S. Pat. No. 5,290,816. U.S. Pat. No. 4,812, 446 describes capsaicin analogs and methods for their preparation. Furthermore, U.S. Pat. No. 4,424,205 cites Newman, "Natural and Synthetic Pepper-Flavored Substances," published in 1954 as listing pungency of capsaicin-like analogs. Ton et al., *British Journal of Pharmacology* 10:175-182 (1955), discusses pharmacological actions of capsaicin and its analogs.

With the inclusion of an irritant (e.g., capsaicin) in the dosage form, the irritant imparts a burning or discomforting quality to the abuser to discourage the inhalation, injection, or oral administration of the tampered dosage form, and preferably to prevent the abuse of the dosage form. Suitable capsaicin compositions include capsaicin (trans 8-methyl-N-vanillyl-6-noneamide) or analogues thereof in a concentration between about 0.00125% and 50% by weight, preferably between about 1% and about 7.5% by weight, and most preferably, between about 1% and about 5% by weight.

The aversive agent can comprise a single type of aversive agent (e.g., a capsaicin), multiple forms of a single type of aversive agent (e.g., a capasin and an analogue thereof), or a combination of different types of aversive agents (e.g., one or more bittering agents and one or more gelling agents). Desirably, the amount of aversive agent in the sequestering subunit of the invention is not toxic to the host.

The sequestering subunit of the invention can have a blocking agent that is a tether to which the aversive agent is attached. The term "tether" as used herein refers to any means by which the aversive agent is tethered or attached to the interior of the sequestering subunit, such that the aversive agent is not released, unless the sequestering subunit is tampered with. In this instance, a tether-aversive agent complex is formed. The complex is coated with a tether-impermeable material, thereby substantially preventing release of the aversive agent from the subunit. The term "tether-impermeable material" as used herein refers to any material that substantially prevents or prevents the tether from permeating through the material. The tether preferably is an ion exchange resin bead.

Methods of making any of the sequestering subunits of the invention are known in the art. See, for example, *Remington: The Science and Practice of Pharmacy*, Alfonso R. Genaro (ed), 20$^{th}$ edition, and Example 2 set forth below. The sequestering subunits can be prepared by any suitable method to provide, for example, beads, pellets, granules, spheroids, and the like.

Spheroids or beads, coated with an active ingredient can be prepared, for example, by dissolving the active ingredient in water and then spraying the solution onto a substrate, for example, nu pariel 18/20 beads, using a Wurster insert. Optionally, additional ingredients are also added prior to coating the beads in order to assist the active ingredient in binding to the substrates, and/or to color the solution; etc. The resulting substrate-active material optionally can be overcoated with a barrier material to separate the therapeutically active agent from the next coat of material, e.g., release-retarding material. Preferably, the barrier material is a material comprising hydroxypropyl methylcellulose. However, any film-former known in the art can be used. Preferably, the barrier material does not affect the dissolution rate of the final product.

Pellets comprising an active ingredient can be prepared, for example, by a melt pelletization technique. Typical of such techniques is when the active ingredient in finely divided form is combined with a binder (also in particulate form) and other optional inert ingredients, and thereafter the mixture is pelletized, e.g., by mechanically working the mixture in a high shear mixer to form the pellets (e.g., pellets, granules, spheres, beads; etc., collectively referred to herein as "pellets"). Thereafter, the pellets can be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

The diameter of the extruder aperture or exit port also can be adjusted to vary the thickness of the extruded strands. Furthermore, the exit part of the extruder need not be round; it can be oblong, rectangular; etc. The exiting strands can be reduced to particles using a hot wire cutter, guillotine; etc.

The melt-extruded multiparticulate system can be, for example, in the form of granules, spheroids, pellets, or the like, depending upon the extruder exit orifice. The terms "melt-extruded multiparticulate(s)" and "melt-extruded multiparticulate system(s)" and "melt-extruded particles" are used interchangeably herein and include a plurality of sub-units, preferably within a range of similar size and/or shape. The melt-extruded multiparticulates are preferably in a range of from about 0.1 to about 12 mm in length and have a diameter of from about 0.1 to about 5 mm. In addition, the melt-extruded multiparticulates can be any geometrical shape within this size range. Alternatively, the extrudate can simply be cut into desired lengths and divided into unit doses of the therapeutically active agent without the need of a spheronization step.

The substrate also can be prepared via a granulation technique. Generally, melt-granulation techniques involve melting a normally solid hydrophobic material, e.g., a wax, and incorporating an active ingredient therein. To obtain a sustained-release dosage form, it can be necessary to incorporate an additional hydrophobic material.

A coating composition can be applied onto a substrate by spraying it onto the substrate using any suitable spray equipment. For example, a Wuster fluidized-bed system can be used in which an air flow from underneath, fluidizes the coated material and effects drying, while the insoluble polymer coating is sprayed on. The thickness of the coating will depend on the characteristics of the particular coating composition, and can be determined by using routine experimentation.

Any manner of preparing a subunit can be employed. By way of example, a subunit in the form of a pellet or the like can be prepared by co-extruding a material comprising the opioid agonist and a material comprising the opioid antagonist and/or aversive agent in sequestered form. Optionally, the opioid agonist composition can cover, e.g., overcoat, the material comprising the antagonist and/or aversive agent in sequestered form. A bead, for example, can be prepared by coating a substrate comprising an opioid antagonist and/or an aversive agent in sequestered form with a solution comprising an opioid agonist.

The sequestering subunits of the invention are particularly well-suited for use in compositions comprising the sequestering subunit and a therapeutic agent in releasable form. In this regard, the invention also provides a composition comprising any of the sequestering subunits of the invention and a therapeutic agent in releasable form. By "releasable form" is meant to include immediate release, intermediate release, and sustained-release forms. The therapeutic agent can be formulated to provide immediate release of the therapeutic agent. In preferred embodiments, the composition provides sustained-release of the therapeutic agent.

The therapeutic agent in sustained-release form is preferably a particle of therapeutic agent that is combined with a release-retarding material. The release-retarding material is preferably a material that permits release of the therapeutic agent at a sustained rate in an aqueous medium. The release-retarding material can be selectively chosen so as to achieve, in combination with the other stated properties, a desired in vitro release rate.

In a preferred embodiment, the oral dosage form of the invention can be formulated to provide for an increased duration of therapeutic action allowing once-daily dosing. In general, a release-retarding material is used to provide the increased duration of therapeutic action. Preferably, the once-daily dosing is provided by the dosage forms and methods described in U.S. Patent Application Ser. No. 10/667,570 to Boehm, entitled "Sustained-Release Opioid Formulations and Method of Use," filed on Sep. 22, 2003, and incorporated herein by reference.

Preferred release-retarding materials include acrylic polymers, alkylcelluloses, shellac, zein, hydrogenated vegetable oil, hydrogenated castor oil, and combinations thereof. In certain preferred embodiments, the release-retarding material is a pharmaceutically acceptable acrylic polymer, including acrylic acid and methacrylic acid copolymers, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, and glycidyl methacrylate copolymers. In certain preferred embodiments, the acrylic polymer comprises one or more ammonio methacrylate copolymers. Ammonio methacrylate copolymers are well-known in the art, and are described in NF21, the 21$^{st}$ edition of the National Formulary, published by the United States Pharmacopeial Convention Inc. (Rockville, Md.), as fully polymerized copolymers of acrylic and methacrylic acid esters with a low content of quaternary ammonium groups. In other preferred embodiments, the release-retarding material is an alkyl cellulosic material, such as ethylcellulose. Those skilled in the art will appreciate that other cellulosic polymers, including other alkyl cellulosic polymers, can be substituted for part or all of the ethylcellulose.

Release-modifying agents, which affect the release properties of the release-retarding material, also can be used. In a preferred embodiment, the release-modifying agent functions as a pore-former. The pore-former can be organic or inorganic, and include materials that can be dissolved, extracted or leached from the coating in the environment of use. The pore-former can comprise one or more hydrophilic polymers, such as hydroxypropylmethylcellulose. In certain preferred embodiments, the release-modifying agent is selected from hydroxypropylmethylcellulose, lactose, metal stearates, and combinations thereof.

The release-retarding material can also include an erosion-promoting agent, such as starch and gums; a release-modifying agent useful for making microporous lamina in the environment of use, such as polycarbonates comprised of linear polyesters of carbonic acid in which carbonate groups reoccur in the polymer chain; and/or a semi-permeable polymer.

The release-retarding material can also include an exit means comprising at least one passageway, orifice, or the like. The passageway can be formed by such methods as those disclosed in U.S. Pat. Nos. 3,845,770; 3,916,889; 4,063,064; and 4,088,864, which are incorporated herein by reference. The passageway can have any shape, such as round, triangular, square, elliptical, irregular; etc.

In certain embodiments, the therapeutic agent in sustained-release form can include a plurality of substrates comprising the active ingredient, which substrates are coated with a sustained-release coating comprising a release-retarding material.

The sustained-release preparations of the invention can be made in conjunction with any multiparticulate system, such as beads, ion-exchange resin beads, spheroids, microspheres, seeds, pellets, granules, and other multiparticulate systems in order to obtain a desired sustained-release of the therapeutic agent. The multiparticulate system can be presented in a capsule or in any other suitable unit dosage form.

In certain preferred embodiments, more than one multiparticulate system can be used, each exhibiting different characteristics, such as pH dependence of release, time for release in various media (e.g., acid, base, simulated intestinal fluid), release in vivo, size and composition.

To obtain a sustained-release of the therapeutic agent in a manner sufficient to provide a therapeutic effect for the sustained durations, the therapeutic agent can be coated with an amount of release-retarding material sufficient to obtain a weight gain level from about 2 to about 30%, although the coat can be greater or lesser depending upon the physical properties of the particular therapeutic agent utilized and the desired release rate, among other things. Moreover, there can be more than one release-retarding material used in the coat, as well as various other pharmaceutical excipients.

Solvents typically used for the release-retarding material include pharmaceutically acceptable solvents, such as water, methanol, ethanol, methylene chloride and combinations thereof.

In certain embodiments of the invention, the release-retarding material is in the form of a coating comprising an aqueous dispersion of a hydrophobic polymer. The inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentrations of the plasticizer, however, can be determined by routine experimentation.

Examples of plasticizers for ethylcellulose and other celluloses include dibutyl sebacate, diethyl phthalate, triethyl citrate, tributyl citrate, and triacetin, although it is possible that other plasticizers (such as acetylated monoglycerides, phthalate esters, castor oil; etc.) can be used.

Examples of plasticizers for the acrylic polymers include citric acid esters, such as triethyl citrate NF21, tributyl citrate, dibutyl phthalate, and possibly 1,2-propylene glycol, polyethylene glycols, propylene glycol, diethyl phthalate, castor oil, and triacetin, although it is possible that other plasticizers (such as acetylated monoglycerides, phthalate esters, castor oil; etc.) can be used.

The sustained-release profile of drug release in the formulations of the invention (either in vivo or in vitro) can be altered, for example, by using more than one release-retarding material, varying the thickness of the release-retarding material, changing the particular release-retarding material used, altering the relative amounts of release-retarding material, altering the manner in which the plasticizer is added (e.g., when the sustained-release coating is derived from an aqueous dispersion of hydrophobic polymer), by varying the amount of plasticizer relative to retardant material, by the inclusion of additional ingredients or excipients, by altering the method of manufacture; etc.

In certain other embodiments, the oral dosage form can utilize a multiparticulate sustained-release matrix.

In certain embodiments, the sustained-release matrix comprises a hydrophilic and/or hydrophobic polymer, such as gums, cellulose ethers, acrylic resins and protein-derived materials. Of these polymers, the cellulose ethers, specifically hydroxyalkylcelluloses and carboxyalkylcelluloses, are preferred. The oral dosage form can contain between about 1% and about 80% (by weight) of at least one hydrophilic or hydrophobic polymer.

The hydrophobic material is preferably selected from the group consisting of alkylcellulose, acrylic and methacrylic acid polymers and copolymers, shellac, zein, hydrogenated castor oil, hydrogenated vegetable oil, or mixtures thereof. Preferably, the hydrophobic material is a pharmaceutically acceptable acrylic polymer, including acrylic acid and methacrylic acid copolymers, methyl methacrylate, methyl methacrylate copolymers, ethoxyethyl methacrylates, cyanoethyl methacrylate, aminoalkyl methacrylate copolymer, poly (acrylicacid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material can also include hydroxyalkylcelluloses such as hydroxypropylmethylcellulose and mixtures of the foregoing.

Preferred hydrophobic materials are water-insoluble with more or less pronounced hydrophobic trends. Preferably, the hydrophobic material has a melting point from about 30° C. to about 200° C., more preferably from about 45° C. to about 90° C. The hydrophobic material can include neutral or synthetic waxes, fatty alcohols (such as lauryl, myristyl, stearyl, cetyl or preferably cetostearyl alcohol), fatty acids, including fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include beeswax, glycowax, castor wax, carnauba wax and wax-like substances, e.g., material normally solid at room temperature and having a melting point of from about 30° C. to about 100° C.

Preferably, a combination of two or more hydrophobic materials are included in the matrix formulations. If an additional hydrophobic material is included, it is preferably a natural or synthetic wax, a fatty acid, a fatty alcohol, or mixtures thereof. Examples include beeswax, carnauba wax, stearic acid and stearyl alcohol.

In other embodiments, the sustained-release matrix comprises digestible, long-chain (e.g., $C_8$-$C_{50}$, preferably $C_{12}$-$C_{40}$), substituted or unsubstituted hydrocarbons, such as fatty acids, fatty alcohols, glyceryl esters of fatty acids, mineral and vegetable oils and waxes. Hydrocarbons having a melting point of between about 25° C. and about 90° C. are preferred. Of these long-chain hydrocarbon materials, fatty (aliphatic) alcohols are preferred. The oral dosage form can contain up to about 60% (by weight) of at least one digestible, long-chain hydrocarbon.

Further, the sustained-release matrix can contain up to 60% (by weight) of at least one polyalkylene glycol.

In a preferred embodiment, the matrix comprises at least one water-soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$-$C_6$) alkyl cellulose, such as hydroxypropylcellulose, hydroxypropylmethylcellulose and, preferably, hydroxyethyl cellulose. The amount of the at least one hydroxyalkyl cellulose in the oral dosage form will be determined, amongst other things, by the precise rate of opioid release required. The amount of the at least one aliphatic alcohol in the present oral dosage form will be determined by the precise rate of opioid release required. However, it will also depend on whether the at least one polyalkylene glycol is absent from the oral dosage form.

In certain embodiments, a spheronizing agent, together with the active ingredient, can be spheronized to form spheroids. Microcrystalline cellulose and hydrous lactose impalpable are examples of such agents. Additionally (or alternatively), the spheroids can contain a water-insoluble polymer, preferably an acrylic polymer, an acrylic copolymer, such as a methacrylic acid-ethyl acrylate copolymer, or ethyl cellulose. In such embodiments, the sustained-release coating will generally include a water-insoluble material such as (a) a wax, either alone or in admixture with a fatty alcohol, or (b) shellac or zein.

Preferably, the sequestering subunit comprises the therapeutic agent in sustained-release form. The sustained-release subunit can be prepared by any suitable method. For example, a plasticized aqueous dispersion of the release-retarding material can be applied onto the subunit comprising the opioid agonist. A sufficient amount of the aqueous dispersion of release-retarding material to obtain a predetermined sustained-release of the opioid agonist when the coated substrate is exposed to aqueous solutions, e.g., gastric fluid, is preferably applied, taking into account the physical characteristics of the opioid agonist, the manner of incorporation of the plasticizer; etc. Optionally, a further overcoat of a film-former, such as Opadry (Colorcon, West Point, Va.), can be applied after coating with the release-retarding material.

The subunit can be cured in order to obtain a stabilized release rate of the therapeutic agent. In embodiments employing an acrylic coating, a stabilized product can be preferably obtained by subjecting the subunit to oven curing at a temperature above the glass transition temperature of the plasticized acrylic polymer for the required time period. The optimum temperature and time for the particular formulation can be determined by routine experimentation.

Once prepared, the subunit can be combined with at least one additional subunit and, optionally, other excipients or drugs to provide an oral dosage form.

In addition to the above ingredients, a sustained-release matrix also can contain suitable quantities of other materials, e.g., diluents, lubricants, binders, granulating aids, colorants, flavorants and glidants that are conventional in the pharmaceutical art.

Optionally and preferably, the mechanical fragility of any of the sequestering subunits described herein is the same as the mechanical fragility of the therapeutic agent in releasable form. In this regard, tampering with the composition of the invention in a manner to obtain the therapeutic agent will result in the destruction of the sequestering subunit, such that the aversive agent is released and mixed in with the therapeutic agent. Consequently, the aversive agent cannot be separated from the therapeutic agent, and the therapeutic agent cannot be administered in the absence of the aversive agent. Methods of assaying the mechanical fragility of the sequestering subunit and of a therapeutic agent are known in the art. See, for example, Example 3 set forth below.

The therapeutic agent of the present inventive compositions can be any medicinal agent used for the treatment of a condition or disease, a pharmaceutically acceptable salt thereof, or an analogue of either of the foregoing. The therapeutic agent can be, for example, an analgesic (e.g., an opioid agonist, aspirin, acetaminophen, non-steroidal anti-inflammatory drugs ("NSAIDS"), N-methyl-D-aspartate ("NMDA") receptor antagonists, cyclooxygenase-II inhibitors ("COX-II inhibitors"), and glycine receptor antagonists), an antibacterial agent, an anti-viral agent, an anti-microbial agent, anti-infective agent, a chemotherapeutic, an immunosuppressant agent, an antitussive, an expectorant, a decongestant, an antihistamine drugs, a decongestant, antihistamine drugs, and the like. Preferably, the therapeutic agent is one that is addictive (physically and/or psychologically) upon repeated use and typically leads to abuse of the therapeutic agent. In this regard, the therapeutic agent can be any opioid agonist as discussed herein.

Exemplary NSAIDS include ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well-known.

Exemplary NMDA receptor antagonists include morphinans, such as dexotromethorphan or dextrophan, ketamine, d-methadone, and pharmaceutically acceptable salts thereof, and encompass drugs that block a major intracellular consequence of NMDA-receptor activation, e.g., a ganglioside, such as (6-aminohexyl)-5-chloro-1-naphthalenesulfonamide. These drugs are stated to inhibit the development of tolerance to and/or dependence on addictive drugs, e.g., narcotic analgesics, such as morphine, codeine; etc., in U.S. Pat. Nos. 5,321,012 and 5,556,838 (both to Mayer et al.), both of which are incorporated herein by reference, and to treat chronic pain in U.S. Pat. No. 5,502,058 (Mayer et al.), incorporated herein by reference. The NMDA agonist can be included alone or in combination with a local anesthetic, such as lidocaine, as described in these patents by Mayer et al.

COX-2 inhibitors have been reported in the art, and many chemical compounds are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422, 5,510,368; 5,436,265; 5,409,944 and 5,130,311, all of which are incorporated herein by reference. Certain preferred COX-2 inhibitors include celecoxib (SC-58635), DUP-697, flosulide (CGP-28238), meloxicam, 6-methoxy-2-naphthylacetic acid (6-NMA), MK-966 (also known as Vioxx), nabumetone (prodrug for 6-MNA), nimesulide, NS-398, SC-5766, SC-58215, T-614, or combinations thereof. Dosage levels of COX-2 inhibitor on the order of from about 0.005 mg to about 140 mg per kilogram of body weight per day have been shown to be therapeutically effective in combination with an opioid analgesic. Alternatively, about 0.25 mg to about 7 g per patient per day of a COX-2 inhibitor can be administered in combination with an opioid analgesic.

The treatment of chronic pain via the use of glycine receptor antagonists and the identification of such drugs is described in U.S. Pat. No. 5,514,680 (Weber et al.), which is incorporated herein by reference.

Pharmaceutically acceptable salts of the therapeutic agents discussed herein include metal salts, such as sodium salt, potassium salt, cesium salt, and the like; alkaline earth metals, such as calcium salt, magnesium salt, and the like; organic amine salts, such as triethylamine salt, pyridine salt, picoline salt, ethanolamine salt, triethanolamine salt, dicyclohexylamine salt, N,N'-dibenzylethylenediamine salt, and the like; inorganic acid salts, such as hydrochloride, hydrobromide, sulfate, phosphate, and the like; organic acid salts, such as formate, acetate, trifluoroacetate, maleate, tartrate, and the like; sulfonates, such as methanesulfonate, benzenesulfonate, p-toluenesulfonate, and the like; amino acid salts, such as arginate, asparginate, glutamate, and the like.

The composition of the invention can contain more than one therapeutic agent to provide a substantially equivalent therapeutic effect. Alternatively, the dosage form can contain molar equivalent amounts of other salts of the therapeutic agents useful in the invention. By way of example, a combination of two opioid agonists can be included in the dosage form. Thus, in certain embodiments, a combination of two opioid agonists can be included in the same subunit, in addition to the opioid antagonist and/or aversive agent. For example, the subunit can include two opioid agonists having different properties, such as half-life, solubility, potency, and a combination of any of the foregoing. Further, the dosage form can include subunits comprising different opioid agonists or the subunits can be dispersed in a matrix comprising different opioid agonists. In further embodiments, the oral dosage form comprises an opioid agonist and an aversive agent in sequestered form, and, optionally, an opioid antagonist in sequestered form, wherein the aversive agent and opioid agonist are not part of the same subunit.

The composition of the invention can be in any suitable dosage form or formulation, (see, e.g., *Pharmaceutics and Pharmacy Practice*, J. B. Lippincott Company, Philadelphia, Pa., Banker and Chalmers, eds., pages 238-250 (1982)).

Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

One of ordinary skill in the art will readily appreciate that the compositions of the invention can be modified in any number of ways, such that the therapeutic efficacy of the composition is increased through the modification. For instance, the therapeutic agent or sequestering subunit could be conjugated either directly or indirectly through a linker to a targeting moiety. The practice of conjugating therapeutic agents or sequestering subunits to targeting moieties is known in the art. See, for instance, Wadwa et al., *J. Drug Targeting* 3: 111 (1995), and U.S. Pat. No. 5,087,616. The term "targeting moiety" as used herein, refers to any molecule or agent that specifically recognizes and binds to a cell-surface receptor, such that the targeting moiety directs the delivery of the therapeutic agent or sequestering subunit to a population of cells on which the receptor is expressed. Targeting moieties include, but are not limited to, antibodies, or fragments thereof, peptides, hormones, growth factors, cytokines, and any other naturally- or non-naturally-existing ligands, which bind to cell-surface receptors. The term "linker" as used herein, refers to any agent or molecule that bridges the therapeutic agent or sequestering subunit to the targeting moiety. One of ordinary skill in the art recognizes that sites on the therapeutic agent or sequestering subunit, which are not necessary for the function of the agent or sequestering subunit, are ideal sites for attaching a linker and/or a targeting moiety, provided that the linker and/or targeting moiety, once attached to the agent or sequestering subunit, do(es) not interfere with the function of the therapeutic agent or sequestering subunit.

With respect to the present inventive compositions, the composition is preferably an oral dosage form. By "oral dosage form" is meant to include a unit dosage form prescribed or intended for oral administration comprising subunits. Desirably, the composition comprises the sequestering subunit coated with the therapeutic agent in releasable form, thereby forming a composite subunit comprising the sequestering subunit and the therapeutic agent. Accordingly, the invention further provides a capsule suitable for oral administration comprising a plurality of such composite subunits.

Alternatively, the oral dosage form can comprise any of the sequestering subunits of the invention in combination with a therapeutic agent subunit, wherein the therapeutic agent subunit comprises the therapeutic agent in releasable form. In this respect, the invention provides a capsule suitable for oral administration comprising a plurality of sequestering subunits of the invention and a plurality of therapeutic subunits, each of which comprises a therapeutic agent in releasable form.

The invention further provides tablets comprising a sequestering subunit of the invention and a therapeutic agent in releasable form. For instance, the invention provides a tablet suitable for oral administration comprising a first layer comprising any of the sequestering subunits of the invention and a second layer comprising therapeutic agent in releasable form, wherein the first layer is coated with the second layer. The first layer can comprise a plurality of sequestering subunits. Alternatively, the first layer can be or can consist of a single sequestering subunit. The therapeutic agent in releasable form can be in the form of a therapeutic agent subunit and the second layer can comprise a plurality of therapeutic subunits. Alternatively, the second layer can comprise a single substantially homogeneous layer comprising the therapeutic agent in releasable form.

The invention further provides a tablet suitable for oral administration comprising a single layer comprising a therapeutic agent in releasable form and a plurality of any of the sequestering subunits of the invention dispersed throughout the layer of the therapeutic agent in releasable form. The invention also provides a tablet in which the therapeutic agent in releasable form is in the form of a therapeutic agent subunit and the tablet comprises an at least substantially homogeneous mixture of a plurality of sequestering subunits and a plurality of subunits comprising the therapeutic agent.

In preferred embodiments, oral dosage forms are prepared to include an effective amount of melt-extruded subunits in the form of multiparticles within a capsule. For example, a plurality of the melt-extruded multiparticulates can be placed in a gelatin capsule in an amount sufficient to provide an effective release dose when ingested and contacted by gastric fluid.

In another preferred embodiment, the subunits, e.g., in the form of multiparticulates, can be compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Aurther Osol., editor), 1553-1593 (1980), which is incorporated herein by reference. Excipients in tablet formulation can include, for example, an inert diluent such as lactose, granulating and disintegrating agents, such as cornstarch, binding agents, such as starch, and lubricating agents, such as magnesium stearate.

In yet another preferred embodiment, the subunits are added during the extrusion process and the extrudate can be shaped into tablets as set forth in U.S. Pat. No. 4,957,681 (Klimesch et al.), which is incorporated herein by reference.

Optionally, the sustained-release, melt-extruded, multiparticulate systems or tablets can be coated, or the gelatin capsule can be further coated, with a sustained-release coating, such as the sustained-release coatings described herein. Such coatings are particularly useful when the subunit comprises an opioid agonist in releasable form, but not in sustained-release form. The coatings preferably include a sufficient amount of a hydrophobic material to obtain a weight gain level form about 2 to about 30 percent, although the overcoat can be greater, depending upon the physical properties of the particular opioid analgesic utilized and the desired release rate, among other things.

The melt-extruded dosage forms can further include combinations of melt-extruded multiparticulates containing one or more of the therapeutically active agents before being encapsulated. Furthermore, the dosage forms can also include an amount of an immediate release therapeutic agent for prompt therapeutic effect. The immediate release therapeutic agent can be incorporated or coated on the surface of the subunits after preparation of the dosage forms (e.g., controlled-release coating or matrix-based). The dosage forms can also contain a combination of controlled-release beads and matrix multiparticulates to achieve a desired effect.

The sustained-release formulations preferably slowly release the therapeutic agent, e.g., when ingested and exposed to gastric fluids, and then to intestinal fluids. The sustained-release profile of the melt-extruded formulations can be altered, for example, by varying the amount of retardant, e.g., hydrophobic material, by varying the amount of plasticizer relative to hydrophobic material, by the inclusion of additional ingredients or excipients, by altering the method of manufacture; etc.

In other embodiments, the melt-extruded material is prepared without the inclusion of the subunits, which are added thereafter to the extrudate. Such formulations can have the subunits and other drugs blended together with the extruded matrix material, and then the mixture is tableted in order to provide a slow release of the therapeutic agent or other drugs. Such formulations can be particularly advantageous, for example, when the therapeutically active agent included in the formulation is sensitive to temperatures needed for softening the hydrophobic material and/or the retardant material.

In certain embodiments, the release of the aversive agent of the sequestering subunit or composition is expressed in terms of a ratio of the release achieved after tampering, e.g., by crushing or chewing, relative to the amount released from the intact formulation. The ratio is, therefore, expressed as [Crushed]:[Whole], and it is desired that this ratio have a numerical range of at least about 4:1 or greater (e.g., crushed release within 1 hour/intact release in 24 hours). In certain embodiments, the ratio of the therapeutic agent and the aversive agent, present in the sequestering subunit, is about 1:1 to about 50:1 by weight, preferably about 1:1 to about 20:1 by weight or 15:1 to about 30:1 by weight. The weight ratio of the therapeutic agent to aversive agent refers to the weight of the active ingredients. Thus, for example, the weight of the therapeutic agent excludes the weight of the coating, matrix, or other component that renders the aversive agent sequestered, or other possible excipients associated with the aversive agent particles. In certain preferred embodiments, the ratio is about 1:1 to about 10:1 by weight. Because in certain embodiments the aversive agent is in a sequestered from, the amount of such aversive agent within the dosage form can be varied more widely than the therapeutic agent/aversive agent combination dosage forms, where both are available for release upon administration, as the formulation does not depend on differential metabolism or hepatic clearance for proper functioning. For safety reasons, the amount of the aversive agent present in a substantially non-releasable form is selected as not to be harmful to humans, even if fully released under conditions of tampering.

The compositions of the invention are particularly well-suited for use in preventing abuse of a therapeutic agent. In this regard, the invention also provides a method of preventing abuse of a therapeutic agent by a host. The method comprises incorporating the therapeutic agent into any of the compositions of the invention. Upon administration of the composition of the invention to the host, the aversive agent is substantially prevented from being released in the gastrointestinal tract for a time period that is greater than 24 hours. However, if the host tampers with the compositions, the sequestering subunit, which is mechanically fragile, will break and thereby allow the aversive agent to be released. Since the mechanical fragility of the sequestering subunit is the same as the therapeutic agent in releasable form, the aversive agent will be mixed with the therapeutic agent, such that separation between the two components is virtually impossible.

The term "host" as used herein refers to any suitable host. Preferably, the host is a mammal. An especially preferred mammal is the human.

EXAMPLES

The following examples further illustrate the invention but, of course, should not be construed as in any way limiting its scope.

Example 1

This example demonstrates multiple sequestered forms of aversive agents of the prior art and how they release substantial amounts of the aversive agent within a 24 hour time period.

A first sequestered form of an aversive agent comprised the following components:

Core Formulation:

| | |
|---|---|
| Naltrexone HCl | 70.0 g |
| Methocel E5P | 5.0 g |
| Sugar spheres (#16-18 mesh) | 700.0 g |
| Ethyl Alcohol (denatured, SDA3A) | 200.0 g |
| Purified Water | 200.0 g |

Film-Coating Formulation:

| | |
|---|---|
| Eudragit RS100 | 140.0 g |
| Triethyl Citrate (TEC) | 14.0 g |
| Ethyl Alcohol | 1260.0 g |

Naltrexone HCl was dissolved in water. An equal volume of denatured alcohol was added. Methocel was added to the above mixture and stirred until it was completely dissolved. The drug layering took place in a rotor processor insert installed in fluid-bed equipment. A coating solution was prepared by dissolving the Eudragit RS100 in Ethyl Alcohol and dissolving the triethyl citrate in the solution. The naltrexone cores (700 g) were than coated with the coating solution up to a 20% weight gain. The coating was performed in a fluid-bed equipped with a Wurster insert.

The release of naltrexone was determined by dissolution testing conducted according to USP26 Chapter <711>. The test used Apparatus 1 (baskets) at 50 rpm, 500 mL of water, 37° C. Samples were drawn and assayed by a HPLC assay procedure. The HPLC assay procedure was as follows.

| | |
|---|---|
| Column: | Symmetry Shield RP8, 5 micron, 4.6 × 150 mm |
| Column Temperature: | 55° C. |
| Mobile Phase: | 0.1M ammonium acetate pH 5.0/acetonitrile 880/120 |
| Flow Rate: | 1.0 mL/minute |
| Injection Volume: | 50 μl |
| Detection: | UV at 281 nm |

As shown in Table 1, the release of naltrexone from a sequestering subunit comprising 20% weight gain of Eudragit RS100/TEC was inhibited to the same extent as the release of naltrexone from a sequestering subunit comprising 16% weight gain of Eudragit RS100/TEC. Specifically, more than 20% of the starting dose of naltrexone was released from either sequestering subunit after 24 hours had elapsed. This indicates that the sequestering unit is unable to substantially prevent the release of the Naltrexone over 24 hours.

TABLE 1

| | % release at indicated timepoint (hours) Time (hours) | | | | |
|---|---|---|---|---|---|
| | 5 | 10 | 15 | 20 | 24 |
| 16% weight gain | 3.3 | 6.3 | 10.8 | 16.4 | 20.9 |
| 20% weight gain | 7.2 | 12.3 | 17.9 | 22.9 | 26.5 |

A second sequestered form of an aversive agent comprised the following components:
Core Formulation:

| Naltrexone HCl | 70.0 g |
|---|---|
| Methocel E5P | 5.0 g |
| Sugar spheres (#16-18 mesh) | 700.0 g |
| Ethyl alcohol (denatured, SDA3A) | 200.0 g |
| Purified Water | 200.0 g |

Film-Coating Formulation:

| Eudragit NE 30D | 500.0 g |
|---|---|
| Triethyl Citrate (TEC) | 150.0 g |
| Ethyl Alcohol | 1260.0 g |

The sequestering subunit was made by the same process as the first sequestering subunit. The release of naltrexone was assayed in the same manner as above.

As shown in Table 2, the release of naltrexone from a sequestering subunit comprising 20% weight gain of Eudragit NE30D/TEC was inhibited to a similar extent as the release of naltrexone from a sequestering subunit comprising 16% weight gain of Eudragit NE30D/TEC. Specifically, about 80% of the starting dose of naltrexone was released from either sequestering subunit after 20 hours had elapsed. This indicates that the sequestering unit is unable to substantially prevent the release of the Naltrexone over 24 hours.

TABLE 2

| | % release at indicated timepoint (hours) Time (hours) | | | | |
|---|---|---|---|---|---|
| | 5 | 10 | 15 | 20 | 24 |
| 16% weight gain | 60 | 76.5 | 83.5 | 82.9 | N/D |
| 20% weight gain | 48.3 | 69.1 | 78.5 | 78.7 | N/D |

N/D = not determined

A third sequestered form of an aversive agent comprised the following components:
Core Formulation:

| Naltrexone HCl | 70.0 g |
|---|---|
| Methocel E5P | 5.0 g |
| Sugar spheres (#16-18 mesh) | 700.0 g |
| Ethyl Alcohol (denatured, SDA3A) | 200.0 g |
| Purified Water | 200.0 g |

Film-Coating Formulation:

| Ethyl Cellulose N10 | 126.0 g |
|---|---|
| Dibutyl Sebacate (DBS) | 14.0 g |
| Ethyl Alcohol | 1260.0 g |

The sequestering subunit was made in accordance with the above method. The release of naltrexone was also assayed in the same manner as above.

As shown in Table 3, 100% of the starting dose of naltrexone was released from the sequestering subunit after 20 hours had elapsed. The percentage weight gain did not significantly affect the release of naltrexone. This indicates that the sequestering unit is unable to substantially prevent the release of the Naltrexone over 24 hours.

TABLE 3

| | % release at indicated timepoint (hours) Time (hours) | | | | |
|---|---|---|---|---|---|
| | 5 | 10 | 15 | 20 | 24 |
| 12% weight gain | 39.0 | 60.3 | 77.9 | 99.6 | N/D |
| 16% weight gain | 36.4 | 60.1 | 80.5 | 108.8 | N/D |
| 20% weight gain | 29.2 | 52.3 | 71.1 | 95.7 | N/D |

N/D = not determined

A fourth sequestered form of an aversive agent comprised the following components:
Core Formulation:

| Naltrexone HCl | 115.0 g |
|---|---|
| Plasdone K29/32 | 115.0 g |
| Sugar spheres (18-20 mesh) | 1930.0 g |
| Ethyl Alcohol | 651.0 g |
| Purified Water | 651.0 g |

Film-Coating Formulation:

| Eudragit RS100 | 189.0 g |
|---|---|
| Dibutyl Sebacate | 21.0 g |
| Ethyl Alcohol | 2590.0 g |

The sequestering subunit was made in accordance with the above method. The release of naltrexone was also assayed in the same manner as above.

As shown in Table 4, coatings that provided a 25% weight gain of the sequestering subunit demonstrated the least amount of release of naltrexone. Specifically, 23.3% of the starting amount was released in 24 hours. In contrast, the sequestering subunit comprising a coating, which provided a 12% weight gain, released about 90% of the starting amount of naltrexone. This indicates that the sequestering unit is unable to substantially prevent the release of the naltrexone over 24 hours at any of these applied coat weights. Even at 25% weight gain, the sequestering subunit is unable to prevent the release of more than 20% of the Naltrexone at 24 hours.

TABLE 4

| | % release at indicated timepoint (hours) Time (hours) | | | | |
|---|---|---|---|---|---|
| | 5 | 10 | 15 | 20 | 24 |
| 12% weight gain | 27.3 | 58.9 | 75.0 | 84.7 | 89.7 |
| 16% weight gain | 11.6 | 32.1 | 48.2 | 31.2 | 70.0 |
| 20% weight gain | 5.2 | 20.3 | 27.5 | 35.2 | 43.4 |
| 25% weight gain | 2.5 | 12.8 | 17.0 | 20.2 | 23.3 |

A fifth sequestered form of an aversive agent comprised the following components:

| | Amount per unit (mg) |
|---|---|
| Caffeine | 5.0 |
| Sugar Spheres (#16-18 mesh) | 94.6 |
| Hypromellose | 0.4 |
| Ethylcellulose | 7.9 |
| Dibutyl Sebacate | 1.6 |
| Magnesium Stearate | 1.6 |
| Total | 111.1 |

Caffeine was dispersed in a hydroalcoholic solution of hypromellose with a mechanical stirrer. The resulting dispersion was layered onto sugar spheres using a rotor granulation process in Glatt GPCG-3 fluid-bed. A polymer solution of ethylcellulose and dibutyl sebacate in ethanol was prepared, and magnesium stearate was dispersed into the polymer solution just prior to spraying. The polymer dispersion was then coated onto caffeine cores in Glatt GPCG-3 with a 4" Wurster insert.

The release of caffeine was determined by dissolution testing conducted according to USP26 Chapter <711>. The test used Apparatus 2 (paddles) at 100 rpm, 900 mL of 0.05M phosphate buffer pH 7.5, 37° C. Samples were drawn and assayed UV absorbance at 273 nm.

As shown in Table 5 (set forth below), 50% of the starting dose of caffeine was released after 10 hours, whereas over 80% of the starting dose of caffeine was released after 17 hours had elapsed. This indicates that the sequestering unit is unable to substantially prevent the release of the caffeine over 24 hours.

A sixth sequestered form of an aversive agent comprised the following components:

| | Amount per unit (mg) |
|---|---|
| Caffeine | 5.0 |
| Sugar Spheres (#16-18 mesh) | 94.6 |
| Hypromellose | 0.4 |
| Eudragit RS PO | 8.1 |
| Sodium Lauryl Sulfate | 0.2 |
| Dibutyl Sebacate | 0.8 |
| Magnesium Stearate | 2.0 |
| Total | 111.1 |

Caffeine was dispersed in a hydroalcoholic solution of hypromellose with a mechanical stirrer. The resulting dispersion was layered onto sugar spheres using a rotor granulation process in Glatt GPCG-3 fluid-bed. A polymer solution of Eudragit RS, sodium lauryl sulfate and dibutyl sebacate in ethanol was prepared, and magnesium stearate was dispersed into the polymer solution just prior to spraying. The polymer dispersion was then coated onto caffeine cores in Glatt GPCG-3 with a 4" Wurster insert. The release of caffeine was assayed as described above.

As shown in Table 5, 46% of the starting dose of caffeine was released after 13 hours, whereas over 60% of the starting dose of caffeine was released after 17 hours had elapsed. This indicates that the sequestering unit is unable to substantially prevent the release of the caffeine over 24 hours.

A seventh sequestered form of an aversive agent comprised the following components:

| | Amount per unit (mg) |
|---|---|
| Caffeine | 5.0 |
| Sugar Spheres (#16-18 mesh) | 94.5 |
| Hydroxypropyl Cellulose | 0.5 |
| Ethylcellulose | 9.6 |
| Dibutyl Sebacate | 1.5 |
| Total | 111.1 |

Caffeine was dispersed in an ethanolic solution of hydroxypropyl cellulose using a mechanical stirrer. The resulting dispersion was layered onto sugar spheres using a rotor granulation process in Glatt GPCG-3 fluid-bed. A polymer solution of ethylcellulose and dibutyl sebacate in ethanol was prepared, which was then coated onto caffeine cores in Glatt GPCG-3 with a 4" Wurster insert. The release of caffeine was assayed as described above.

As shown in Table 5, 50% of the starting dose of caffeine was released after 10 hours whereas about 70% of the starting dose of caffeine was released after 17 hours had elapsed. This indicates that the sequestering unit is unable to substantially prevent the release of the caffeine over 24 hours.

An eighth sequestered form of an aversive agent comprised the following components:

| | Amount per unit (mg) |
|---|---|
| Diltiazem HCl | 5.0 |
| Sugar Spheres (#16-18 mesh) | 43.8 |
| Hydroxypropyl Cellulose | 1.3 |
| Ethylcellulose | 10.0 |
| Magnesium Stearate | 1.0 |
| Total | 60.1 |

Diltiazem was dispersed in an ethanolic solution of hydroxypropyl cellulose using a mechanical stirrer. The resulting dispersion was layered onto sugar spheres using a rotor granulation process in Glatt GPCG-3 fluid-bed. A polymer solution of ethylcellulose in ethanol was prepared and magnesium stearate was dispersed just prior to spraying. The polymer dispersion was then coated onto diltiazem cores in Glatt GPCG-3 with a 4" Wurster insert.

The release of diltiazem was assayed as described above for caffeine except that a wavelength of 236 nm was used to assay diltiazem.

As shown in Table 5, 25% of the starting dose of diltiazem was released after about 13 hours had elapsed, whereas about 36% of the starting dose of diltiazem was released after 17 hours had elapsed. This indicates that the sequestering unit is unable to substantially prevent the release of the caffeine over 24 hours.

A ninth sequestered form of an aversive agent comprised the following components:

|  | Amount per unit (mg) |
| --- | --- |
| Diltiazem HCl | 5.0 |
| Sugar Spheres (#20-25 mesh) | 43.8 |
| Hydroxypropyl Cellulose | 1.3 |
| Eudragit RS PO | 7.4 |
| Sodium Lauryl Sulfate | 0.3 |
| Dibutyl Sebacate | 0.7 |
| Magnesium Stearate | 2.5 |
| Total | 60.1 |

Diltiazem was dispersed in a ethanolic solution of hydroxypropyl cellulose with a mechanical stirrer. The resulting dispersion was layered onto sugar spheres using a rotor granulation process in Glatt GPCG-3 fluid-bed. A polymer solution of Eudragit RS, sodium lauryl sulfate and dibutyl sebacate in ethanol was prepared, and magnesium stearate was dispersed into the polymer solution just prior to spraying. The polymer dispersion was then coated onto diltiazem in Glatt GPCG-3 with a 4" Wurster insert. The release of diltiazem was assayed as described above.

As shown in Table 5, more than about 1% of the starting dose of diltiazem was released after about 17 hours had elapsed. This suggests that this sequestering agent is capable of substantially preventing the release of the aversive agent over a period of 17 hours, however, over 20% was released at 24 hours. This suggests that this sequestering agent is unable to substantially prevent the release of diltiazem over a period of 24 hours.

A tenth sequestered form of an aversive agent comprised the following components:

|  | Amount per unit (mg) |
| --- | --- |
| Propranolol HCl | 5.0 |
| Sugar Spheres (#20-25 mesh) | 43.8 |
| Hydroxypropyl Cellulose | 1.3 |
| Eudragit RS PO | 7.4 |
| Sodium Lauryl Sulfate | 0.3 |
| Dibutyl Sebacate | 0.7 |
| Magnesium Stearate | 2.5 |
| Total | 60.1 |

Propranolol was dispersed in a ethanolic solution of hydroxypropyl cellulose with a mechanical stirrer. The resulting dispersion was layered onto sugar spheres using a rotor granulation process in Glatt GPCG-3 fluid-bed. A polymer solution of Eudragit RS, sodium lauryl sulfate and dibutyl sebacate in ethanol was prepared, and magnesium stearate was dispersed into the polymer solution just prior to spraying. The polymer dispersion was then coated onto propranolol cores in GPCG-3 with a 4" Wurster insert. The release of propranolol was assayed as described above for caffeine except that a wavelength of 290 nm was used to assay propranolol.

As shown in Table 5, 50% of the starting dose of propranolol was released after about 17 hours had elapsed, while 80% of the starting dose of propranolol was released after 24 hours had elapsed. This is the same sequestering agent as used in the previous example and this shows that although the two aversive agents used in the previous example and in this example are similar in molecular size and charge, they behave differently with this sequestering agent.

TABLE 5

|  | % release at indicated timepoint (hours) | | | | | |
| --- | --- | --- | --- | --- | --- | --- |
|  | 3 | 6 | 10 | 13 | 17 | 24 |
| 1$^{st}$ intact dosage form | 4 | 13.4 | 49.3 | 69.1 | 82.1 | N/D |
| 2$^{nd}$ intact dosage form | 7 | 15.7 | 31.2 | 46.1 | 64.5 | N/D |
| 3$^{rd}$ intact dosage form | 8.1 | 28.9 | 49.8 | 60.0 | 69.2 | N/D |
| 4$^{th}$ intact dosage form | 0 | 0.2 | 11.7 | 25.4 | 36.5 | N/D |
| 5$^{th}$ intact dosage form | 0.1 | 0.1 | 0.2 | 0.3 | 0.8 | >20 |
| 6$^{th}$ intact dosage form | 1.3 | 0.4 | 0.8 | 7.8 | 55.8 | N/D |

N/D = not determined

This example demonstrates the drawbacks of the sequestered forms of an agent disclosed by the prior art. The fifth dosage form, as shown in Table 5, released greater than 20% within 24 hours.

Example 2

This example demonstrates a sequestering subunit of the invention and a method of making the same.

The sequestering subunit comprised the following components:

|  | % | Weight (g) |
| --- | --- | --- |
| Naltrexone Core | 81.5 | 700.0 |
| Eudragit RS PO | 12.2 | 105.0 |
| Sodium Lauryl Sulphate | 0.4 | 3.5 |
| Magnesium Stearate | 4.6 | 39.9 |
| Dibutyl Sebacate | 1.2 | 10.5 |
| Ethyl Alcohol |  | 541.1 |

This example was manufactured as described in the first form of Example 1 except that the coating had the composition shown in the table above. The coating was applied to a 16% weight gain.

the release of naltrexone was determined as described in the first form of Example 1.

As shown in the table below, the release of naltrexone over 24 hours was only 3.4%, while the release over 48 hours was only 8.1%.

| Timepoint (hours) | % naltrexone released |
| --- | --- |
| 0 | 0 |
| 6 | 0 |
| 12 | 0.4 |
| 16 | 1.7 |
| 20 | 2.6 |
| 24 | 3.4 |
| 48 | 8.1 |

Example 3

This example demonstrates that the mechanical fragility of a sequestering subunit increases when the sequestering subunit is sealed with a hydrophobic polymer, such as Surelease or Eudragit RS30D.

Crushing or fracture strength of sequestered adverse agent containing subunits was measure using the TA.XTPlus Texture Analyser manufactured by Texture Technologies Corporation of Scarsdale, N.Y. This instrument consisted of a movable arm containing a load cell that measured the resistance to movement of the arm. The arm can be raised or lowered over a fixed base and can be equipped with many different kinds of probes. The arm was driven up or down by a stepping motor. The rate of movement of the arm was controlled, and the force measured by the load cell was recorded, by a computer program. To measure the crushing strength of particles of about 1 mm in diameter, the unit was equipped with a 4 mm flat bottom probe. It was programmed to move the arm down at 0.1 mm per second. A measured force of 10 g was used to determine the point of contact with the particle and so measure the height (diameter) of the particle. Once contact was made, the probe continued to move downward with the measured force increasing more of less linearly until the particle fractured, at which point the force measured abruptly decreased. Further movement can detect secondary or tertiary cracking of the particle. The fracture force was the force being applied at the moment of abrupt decrease or cracking. The brittleness was a measure of how far the probe moves to re-contact the particle following cracking.

As shown in Table 6, sugar spheres of about 1 mm in diameter had a fracture (or cracking) force of about 670 g (average of 10 determinations). When sugar spheres were layered with naltrexone, the fracture force decreased by about 100 g. This was likely due to the thin layer of naltrexone not being firmly bonded to the sugar sphere surface and hence cracking away from the sugar sphere surface. This phenomenon is sometimes referred to as "egg shelling" in the art. Sugar spheres coated with either ethylcellulose (Surelease) of acrylic based polymer (Eudragit RS30D) yielded a much stronger fracture force than do uncoated sugar spheres. A force of the magnitude required to fracture these coating was greater than that required to fracture the naltrexone layer.

TABLE 6

| | Fracture Force (g) | Brittleness (mm) | Product Height (mm) |
|---|---|---|---|
| Sugar spheres | 673 | 0.097 | 0.913 |
| Sugar spheres layered with Naltrexone | 575 | 0.073 | 0.903 |
| Sugar spheres sealed with Surelease | 1060 | 0.181 | 0.938 |
| Sugar spheres sealed with Eudragit RS30D | 1065 | 0.139 | 0.948 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A pharmaceutical composition comprising a sequestering subunit comprising naltrexone or a pharmaceutically acceptable salt thereof and a blocking agent comprising a surfactant, wherein the blocking agent substantially prevents release of the naltrexone or a pharmaceutically acceptable salt thereof from the sequestering subunit and the sequestering subunit is overcoated with an opioid agonist or a pharmaceutically acceptable salt thereof in releasable form.

2. The pharmaceutical composition of claim 1 wherein the blocking agent prevents the release of at least about 99% of the naltrexone or a pharmaceutically acceptable salt thereof from the sequestering subunit in the gastrointestinal tract for at least about 12 hours.

3. The pharmaceutical composition of claim 1 wherein the blocking agent prevents the release of at least about 95% of the naltrexone or a pharmaceutically acceptable salt thereof from the sequestering subunit in the gastrointestinal tract for a time period that is greater than 24 hours.

4. The pharmaceutical composition of claim 1 wherein the opioid agonist is selected from the group consisting of morphine, hydromorphone, oxycodone, hydrocodone, and pharmaceutically acceptable salts thereof.

5. The pharmaceutical composition of claim 4 wherein the opioid agonist is morphine or a pharmaceutically acceptable salt thereof.

6. The pharmaceutical composition of claim 1 wherein the surfactant is sodium lauryl sulphate.

7. The pharmaceutical composition of claim 1 wherein the blocking agent comprises Eudragit RS PO and sodium lauryl sulphate, the blocking agent prevents the release of at least about 99% of the naltrexone or a pharmaceutically acceptable salt thereof from the sequestering subunit in the gastrointestinal tract for at least about 12 hours, the blocking agent prevents the release of at least about 95% of the naltrexone or a pharmaceutically acceptable salt thereof from the sequestering subunit in the gastrointestinal tract for a time period that is greater than 24 hours, and the opioid agonist is morphine or a pharmaceutically acceptable salt thereof.

8. A pharmaceutical composition comprising:
   a. a sequestering subunit comprising:
      i. a naltrexone core comprising naltrexone or a pharmaceutically acceptable salt thereof on a substrate; and,
      ii. a coating comprising a hydrophobic material and a surfactant covering the naltrexone core; and,
   b. an overcoat comprising an opioid agonist or a pharmaceutically acceptable salt thereof covering the sequestering subunit.

9. The pharmaceutical composition of claim 8 wherein the substrate is a spheroid or a bead.

10. The pharmaceutical composition of claim 8 wherein the surfactant is sodium lauryl sulphate.

11. The pharmaceutical composition of claim 8 wherein the coating prevents the release of at least about 99% of the naltrexone or a pharmaceutically acceptable salt thereof from the sequestering subunit in the gastrointestinal tract for at least about 12 hours.

12. The pharmaceutical composition of claim 8 wherein the coating prevents the release of at least about 95% of the naltrexone or a pharmaceutically acceptable salt thereof from the sequestering subunit in the gastrointestinal tract for a time period that is greater than 24 hours.

13. The pharmaceutical composition of claim 8 wherein the opioid agonist is selected from the group consisting of morphine, hydromorphone, oxycodone, hydrocodone, and pharmaceutically acceptable salts thereof.

14. The pharmaceutical composition of claim 13 wherein the opioid agonist is morphine or a pharmaceutically acceptable salt thereof.

15. The pharmaceutical composition of claim 8 wherein the blocking agent comprises Eudragit RS PO and sodium lauryl sulphate, the blocking agent prevents the release of at least about 99% of the naltrexone or a pharmaceutically acceptable salt thereof from the sequestering subunit in the gastrointestinal tract for at least about 12 hours, the blocking agent prevents the release of at least about 95% of the naltrexone or a pharmaceutically acceptable salt thereof from the sequestering subunit in the gastrointestinal tract for a time period that is greater than 24 hours, and the opioid agonist is morphine or a pharmaceutically acceptable salt thereof.

16. A sequestering subunit comprising naltrexone or a pharmaceutically acceptable salt thereof and a blocking agent comprising a surfactant wherein the blocking agent prevents the release of at least about 99% of the naltrexone or a pharmaceutically acceptable salt thereof from the sequestering subunit in the gastrointestinal tract for at least about 12 hours and prevents the release of at least about 95% of the naltrexone or a pharmaceutically acceptable salt thereof from the sequestering subunit in the gastrointestinal tract for a time period that is greater than 24 hours.

17. The sequestering subunit of claim 16 wherein the surfactant is sodium lauryl sulphate.

18. The sequestering subunit of claim 16 wherein the blocking agent comprises the surfactant sodium lauryl sulphate and Eudragit RS PO.

* * * * *